US012746281B2

(12) United States Patent

Mohanty et al.

(10) Patent No.: US 12,746,281 B2
(45) Date of Patent: Sep. 29, 2026

(54) AMBIENT TEMPERATURE LIPID PARTICLE STORAGE SYSTEMS AND METHODS

(71) Applicant: Ambient Biosciences, Inc., Ann Arbor, MI (US)

(72) Inventors: Pravansu Mohanty, Ann Arbor, MI (US); Shubhendu Das, Ann Arbor, MI (US); Yolanda Taverner, Ann Arbor, MI (US); Sankar Renu, Ann Arbor, MI (US); Jenny Sharpe, Ann Arbor, MI (US); Laura Bronsart, Ann Arbor, MI (US)

(73) Assignee: AMBIENT BIOSCIENCES INC., Ann Arbor, MI (US)

( * ) Notice: Subject to any disclaimer, the term of this patent is extended or adjusted under 35 U.S.C. 154(b) by 604 days.

(21) Appl. No.: 18/253,077

(22) PCT Filed: Nov. 19, 2021

(86) PCT No.: PCT/US2021/060156
§ 371 (c)(1),
(2) Date: May 16, 2023

(87) PCT Pub. No.: WO2022/109310
PCT Pub. Date: May 27, 2022

(65) Prior Publication Data

US 2024/0009295 A1 Jan. 11, 2024

Related U.S. Application Data

(60) Provisional application No. 63/115,943, filed on Nov. 19, 2020, provisional application No. 63/122,792, filed on Dec. 8, 2020.

(51) Int. Cl.
*A61K 39/12* (2006.01)
*A61K 39/00* (2006.01)

(52) U.S. Cl.
CPC .............. *A61K 39/12* (2013.01); *A61K 39/00* (2013.01); *A61K 2039/5254* (2013.01);
(Continued)

(58) Field of Classification Search
CPC .................... A61K 39/12; A61K 39/00; A61K 2039/5254; A61K 2039/53; A61K 2039/6018; A61K 2039/6031
See application file for complete search history.

(56) References Cited

U.S. PATENT DOCUMENTS

2003/0154729 A1 8/2003 Prien et al.
2009/0004048 A1 1/2009 Elliott et al.
(Continued)

FOREIGN PATENT DOCUMENTS

WO WO 2015/191570 A1 12/2015

OTHER PUBLICATIONS

Zhao, P. et al., Long-term storage of lipid-like nanoparticles for mRNA delivery, Bioactive Materials, 5:. 358-363, Mar. 18, 2020.
(Continued)

*Primary Examiner* — Blessing M Fubara
(74) *Attorney, Agent, or Firm* — Weston R. Gould; Dinsmore & Shohl LLP

(57) ABSTRACT

Disclosed are methods for non-cryogenic vitrification of particles, lipid particles, lipid particle compositions and mRNA vaccine compositions that include a lipid particle, the processes including the steps of providing a lipid particle within a vitrification medium on a capillary network within a desiccation chamber and providing both a heat energy and a lowered atmospheric pressure to provide for rapid vitrification without the vitrification medium or lipid particles experiencing cryogenic temperature or boiling as a result of lowered atmospheric pressure. The lipid particle can be later
(Continued)

reconstituted after long term storage at ambient or higher temperature and still retain structural integrity and activity.

17 Claims, 24 Drawing Sheets

(52) U.S. Cl.
CPC .. *A61K 2039/53* (2013.01); *A61K 2039/6018* (2013.01); *A61K 2039/6031* (2013.01)

(56) References Cited

U.S. PATENT DOCUMENTS

| | | | | |
|---|---|---|---|---|
| 2019/0070117 | A1* | 3/2019 | Genin | F26B 5/06 |
| 2019/0387775 | A1* | 12/2019 | Yamazaki | A23L 7/157 |
| 2020/0068875 | A1* | 3/2020 | Mohanty | C12N 5/546 |

OTHER PUBLICATIONS

Ball, R. et al., Achieving long-term stability of lipid nanoparticles: examining the effect of pH, temperature, and lyophilization, International Journal of Nanomedicine, 12: 305-315, 2017.
Wang, Y., et al., Lyophilized liposome-based parenteral drug development: Reviewing complex product design strategies and current regulatory environments, Advanced Drug Delivery Reviews, 151: 56-71, Mar. 18, 2019.

* cited by examiner

FIG. 13
Relative Fluorescence Units (RFU)
10000
9000
8000
7000
6000
5000
4000
3000
2000
1000
0
Fresh mRNA
Vitrified stored at -20°C
Unvitrified stored at -20°C
Vitrified stored at 28°C
Unvitrified stored at 28°C
Vitrified stored at 55°C
Unvitrified stored at 55°C

A

B

AMBIENT TEMPERATURE LIPID PARTICLE STORAGE SYSTEMS AND METHODS

RELATED APPLICATIONS

This application is a U.S. national stage under 35 U.S.C. § 371 of PCT/US2021/060156 filed Nov. 19, 2021, and which claims priority to U.S. Provisional Application 63/115,943, filed Nov. 19, 2020, and U.S. Provisional Patent Application 63/122,792, filed Dec. 8, 2020, the contents of which are hereby incorporated by reference in their entirety.

FIELD

The present disclosure concerns methods of preparing and storing lipid particles, optionally including within one or more ribonucleic acids, without requirements for cold-chain storage temperatures.

BACKGROUND

Ribonucleic acids, or RNAs, play a key central role in biology providing instrumentation by which the genes encoded in the chromosomes become actuated to expressed proteins. Perhaps the most important ribonucleic acid is the messenger RNA (mRNA) that are assembled as a copy from the parent DNA chromosome, excised for exons and moved to the translation machinery to be read and output as an expressed protein.

This key role in controlling protein output has made mRNA an interesting and compelling point for manipulating a cell or indeed even entire systems within an organism. Of particular interest is manipulating cells to express exogenous genes by proving RNA or producing mutated and/or over-expressed forms of endogenous proteins to affect signaling pathways within the cell and ultimately within a particular tissue or organ.

Providing a cell with an mRNA to an exogenous gene, or a portion or fragment thereof is also a compelling means to prime the immune system of an organism. Forcing a cell to translate a foreign mRNA in vivo can lead to recognition as a foreign body or as an antigen and processing by the cells of the immune system to prepare antibodies and memory cells. If the exogenous gene or fragment thereof is functionally inert when translated but provides for recognition of a pathogen when introduced in the system at a later point, the mRNA has effectively vaccinated an organism without needing or requiring attenuated or live inoculants. mRNA is further comparably safe as it is a non-infectious, non-integrating platform and will be degraded by normal cellular processes. Broadly, mRNA is at the forefront of vaccine development, gene therapy and protein replacement therapies.

While the role and the appeal of mRNA are clear, providing such to subjects has presented a challenge. Initially, concerns centered on delivering mRNA to a cell in vivo effectively. To a large part, that obstacle has been addressed, and while further advances can be expected, the challenge of delivery to a cell in vivo is less (see, e.g., Pardi et al. *Nat. Rev. Drug Discov.* 17: 261-279 (2018)). One key development is the protection of the mRNA prior to transfection into a target cell. This has been addressed in large part by complexing the mRNA with one or more transfection agents, often in the form of lipid particles that encapsulate the mRNA and protect it from degradation.

Now a practicality hurdle presents itself in order to be able to provide mRNA to a swath of the population due to the overall rapid degradation and loss of activity of mRNA or mRNA in a delivery vector at temperatures above freezing. From the point of manufacture up to the point of administration, current techniques require mRNA vaccines, including those packaged into lipid particles, to be maintained at refrigerated temperatures and often well below zero.

Prior methods of storing such systems rely on lyophilization to dry the lipid particles so that content degradation is reduced. This presents a significant expense and demand that frustrate any rapid or voluminous application, particularly due to the large timescales needed to lyophilize these particles. Thus, a need exists in the art to identify ways to store lipid particles that are effective but less demanding.

BRIEF DESCRIPTION OF THE DRAWINGS

The drawings are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present disclosure. Exemplary aspects will become more fully understood from the detailed description and the accompanying drawings, wherein.

DETAILED DESCRIPTION

Figure 1A:
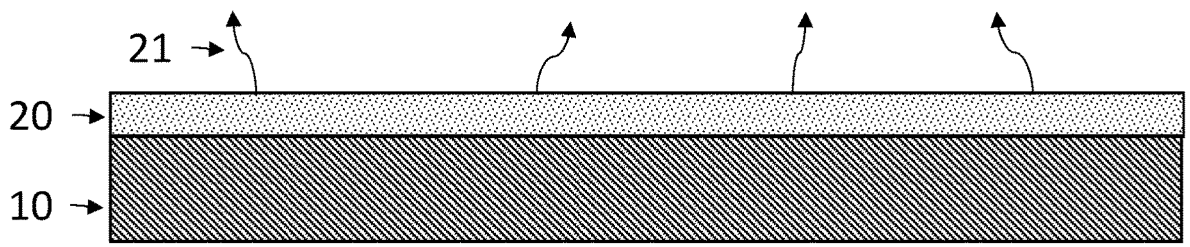
FIG. 1A shows a hydrophilic bed 10 with a thin film of liquid 20 placed a top where the capillary force is significantly higher than the viscous force. This limits the amount of liquid that can be desiccated 21.

The present disclosure concerns methods of preparing lipid particles that alone or including a cargo molecule (e.g. nucleic acid, protein, or other) alone or as packaged in a deliverable vaccine composition that allow for above cryogenic temperature storage while maintaining activity and/or avoiding degradation thereof. The methods further relate to stabilizing mRNA vaccine compositions without freezing or other crystal formation within the sample. The specification is generally directed to mRNA such as those contained within a lipid nanoparticle or virus structure, but such is for illustrative purposes only and are not meant to be limiting. The invention is generally applicable to protecting the structure and stabilizing any cargo within or on a lipid particle.

In some aspects, the present disclosure concerns processes and compositions for preparing and/or storing a particle. In some aspects, the particle may be or include a lipid, protein, carbohydrate, or any combination thereof. In some aspects, the particle may encase or surround a polynucleotide. In some aspects, the particle may include a membrane of lipids, proteins, and/or carbohydrate encasing a polynucleotide. In some aspects, the particle may include a cell encasing a polynucleotide, a virion encasing a polynucleotide and/or a lipid nanoparticle, lipid-like nanoparticle, or liposome encasing a polynucleotide. In some aspects, it will be appreciated that generally a membrane may include lipids along with proteins and/or carbohydrates dispersed therein.

In some aspects, the particles may be or include a membrane of lipids, proteins, and/or carbohydrates that form an encasing. In some aspects, within the encasing may reside a polynucleotide. In further aspects, the particle may be of polynucleotides themselves. In some aspects, the membranes may be a single layer or a bilayer. In some aspects, the membrane may be a synthetic membrane of lipids, proteins, and/or carbohydrates. In some aspects, the particles are of a cellular or cellular derived membrane, such as a plant, bacterial, or animal cell, or of a virion or virion-derived membrane. It will be appreciated that in certain aspects, where a membrane is of a cell or virion, the cell or virion may be attenuated.

In some aspects, the processes and compositions as provided herein include an ionic lipid. In some aspects, the compositions may include lipid nanoparticles (LNPs) or lipid-like nanoparticles (LLNs) that contain at least one nucleic acid molecule or strand therein. The terms "particle" or "lipid particle" as used herein is directed to single or double layer particles that include one or more ionic lipids, optionally but not limited to phosphatidyl choline (PC), phosphatidyl serine (PS), cholesterol, polysaccharide, polymer, protamine, among others. In some aspects, a nucleic acid, protein, or other molecule may be encapsulated within an LNP or LLN of two or more lipids, such as three, four, five or more.

In some aspects, an LNP may include an ionic lipid (usually marked by three sections of an amine head, a linker and a hydrophobic tail, e.g. heptatriaconta-6,9,28,31-tetraen-19-yl 4-(dimethylamino)butanoate (DLin-MC3-DMA or MC3), DLinDMA, and DLin-KC2-DMA). In some aspects, the LNP may include an ionic lipid, a polyethylene glycol and a cholesterol. In further aspects, the LNP may include a combination of an ionic lipid with polyethylene glycol (PEG), cholesterol and/or distearoyl phosphocholine (see, e.g., Sabnis et al., *Mol. Ther.* 26: 1509-1519 (2018); Pardi et al. *J. Exp. Med.* 215:1571-1588 (2018); and, Pardi et al. *J. Control. Release,* 217: 345-351 (2015)). In some aspects, an LNP excludes cholesterol.

In some aspects, the LNP may further include a "helper" lipid. A helper lipid may include 1,2-dioleoyl-3-trimethylammoniumpropane (DOTAP) and/or dioleoylphosphatidylethanolamine (DOPE) and/or lipofectamine and/or dioleoylphosphatidylcholine (DOPC) and/or phosphatidylethanolamine (dioleoyl PE) and/or 3β-[N—(N',N'-dimethylaminoethane)-carbamoyl]-cholesterol (DC-Chol) (see, e.g., Du et al. *Scientific Reports* 4: 7107 (2014) and Cheng et al. *Advanced Drug Delivery Reviews* 99(A): 129-137 (2016)).

Storing particles by methods that include vitrification presents particular challenges due to the nature of the particles themselves. First, the particles typically encapsulate an aqueous environment that, in some aspects, includes one or more functional molecules such as mRNA, protein, etc. The purpose of the particle is to protect the cargo and, in some aspects, promote downstream delivery, targeting, or other functionality to the cargo molecule. Typical prior dry storage methods involve lyophilization that requires timescales on the order of hours to achieve full desiccation and commonly reduces the functional nature of the reconstituted product. This is often the result of the cold temperatures causing a crystallizing of the lipid bilayer that prevents transport of water from the interior of the particle to the exterior during the drying process.

The processes as provided herein are able to achieve full desiccation in minutes, optionally less than 10 minutes while dramatically improving the functionality of the reconstituted product and do not require cold chain storage conditions. The processes do not cause crystallization of the bilayer of the lipid particle allowing transport of water molecules and stabilant though the membrane much more rapidly due to maintaining the membrane in a liquid/gel state that promotes convective transport through the porous layer.

In some aspects, the processes as provided herein maintain the temperature of the particles to near the phase transition temperature (Tc) of the encapsulation layer or particle's membrane. The permeability of liposomes increases when the bilayer transforms from an ordered gel phase to a disordered fluid phase at the Tc. When sufficiently below the Tc, the bilayer forms a more rigid gel phase leading to both reduced fluidity and reduce permeability relative to when the temperature is at the Tc. Similarly, when the temperature is sufficiently above the Tc the fluidity of the membrane increases, but permeability also reduced. Thus, by promoting a temperature of the lipid particle during the desiccation process near the Tc, transport of stabilizing components (e.g. disaccharides) into the particle to stabilize the cargo as well as removal of water from the interior of the particle are both maximized dramatically reducing required desiccation times and dramatically improving storage outcomes by more rapidly and effectively stabilizing both the cargo and the lipid bilayer for subsequent functionality.

While much of this disclosure is directed to protecting and storing mRNA in lipid particles, such is presented as an example only. The processes as provided herein are equally applicable to particles that contain other cargo molecules or combinations of cargo molecules, or may simply be empty particles (no specific cargo molecule). Similarly, the processes are equally applicable to particles of carbohydrates or proteins, other cargo molecules or combinations of cargo molecules or empty particles. Thus, the following description to mRNA and lipid particles is equally applicable to other cargo molecules or empty lipid particles or other particles. Accordingly, recitation of "lipid particle" may equally be interpreted as a particle that incudes a carbohydrate, a protein, a carbohydrate and lipid, a carbohydrate and protein, a lipid and protein, and a lipid/protein/carbohydrate combination.

A "polynucleotide" as provided herein may be used synonymously with nucleic acid and is two or more joined nucleotides (e.g. adenine, guanine, cytosine, thymine, uracil, or any derivative thereof whether naturally occurring or artificial). A polynucleotide may be a DNA, RNA, or other.

As used herein, the term "messenger RNA" or "mRNA" can include a single-stranded ribonucleic acid copy of a gene, including pre-mRNA and mature mRNA, a spliced mRNA, a 5' capped mRNA, an edited mRNA and a polyadenylated mRNA. mRNA can include a gene transcript with introns and exons or a complete gene transcript or a intron-removed or spliced mRNA. mRNA can include single stranded RNA gene transcripts marked by a 5' cap, such as an RNA 7-methylguanosine cap or an RNA $m^7G$ cap. An mRNA may include a start codon of the trimer ATG sequence of bases toward the 5' end of the molecule to signify the initiation for translation of the mRNA segment of interest to a protein and may further include a stop codon of UAA, UAG or UGA that is in frame with the start codon to signify the end of the coding region or the point at which translation is to cease. An mRNA may further include an untranslated region (UTR) following a stop codon and can further include a polyadenylated (poly A) tail after the 3' untranslated region (UTR) of the single stranded molecule. A polyA tail can be provided by the template DNA or by the use of a polyA polymerase. Those skilled in the art will appreciate that the exact length of adenosine in the poly A tail need not be exact but may generally fall within the range of about 100 to about 200 adenosine residues. In some aspects, the mRNA may be optimized to avoid a double-stranded secondary or tertiary structures and/or purified to remove any double-stranded variants (see, e.g., Kariko et al. *Nucleic Acids Res.* 39: e142 (2011)).

As used herein, a "segment of interest" may refer to a span or a sequence of nucleic acids within an mRNA that are to be translated or are capable of being translated within a cell. A segment of interest may be initiated with a start codon and may be terminated by a stop codon, with the stop codon being in the same reading frame (i.e. three nucleic acids to each codon and/amino acid added in the translated protein or peptide). In some aspects, the segment of interest may further feature sequence mutations to replace a rare codon with a synonymous codon with a more abundant cognate tRNA to increase protein production. The segment of interest may further be adapted to enrich G:C content to increase steady state mRNA levels (see, e.g., Kudla et al. *PLoS Biol.* 4: e180 (2006)).

As used herein, a "capped" or a "5' cap" may refer to a structure or modification at the 5' end of an mRNA. In some instances, a cap may be a N7-methylated guanosine linked to the first nucleotide of the mRNA through a reverse 5'-5' triphosphate linker or by binding N7-methylated GTP. In some instances, the first nucleotide is 2'O methylated. In some aspects, a 5' cap may include a synthetic or analog cap, such as an anti-reverse cap analog or a GpppG analog see, e.g. Muttach et al. *Bellstein J Org Chem* 13:2819-2832 (2017); Stepinki et al. *RNA* 7: 1486-1495 (2001); Schalke et al. *RNA Biol.* 9:1319-1330 (2012); and, Malone et al. *Proc. Natl. Acad. USA* 86: 6077-6081 (1989)). A 5' cap may also include the cap, cap1, and/or cap2 structures known in the art. A 5' cap may include commercially available modifications, such as CleanCap. In some aspects, a 5' cap can be applied after transcription through the use of a vaccinia virus capping enzyme.

"Vitrification", as used herein, is a process of converting a material into an amorphous material. The amorphous solid may be free of any crystalline structure.

"Vitrification mixture" as used herein, means a heterogeneous mixture of biological material(s) and/or lipid particles (optionally lipid particles containing one or more biological materials packaged within the lipid particle) and a vitrification medium containing vitrification agents and optionally other materials.

"Vitrification agent," as used herein, is a material that forms an amorphous structure, or that suppress the formation of crystals in other material(s), as the mixture of the vitrification agent and other material(s) cools or desiccates. The vitrification agent(s) may also provide osmotic protection or otherwise enable cell or lipid particle survival during dehydration. In some aspects, the vitrification agent(s) may be any water soluble solution that yields a suitable amorphous structure for storage of biological materials. In other aspects, the vitrification agent may be imbibed within a lipid particle, cell, tissue, or organ.

"Storable or storage," as used herein, refers to a biological material's ability to be preserved and remain viable for use at a later time.

"Hydrophilic," as used herein, means attracting or associating preferentially with water molecules. Hydrophilic materials with a special affinity for water, maximize contact with water and have smaller contact angles with water relative to hydrophobic materials.

"Hydrophobic," as used herein, means lacking affinity for water. Materials that are hydrophobic naturally repel water, causing droplets to form, and have large contact angles with water.

As used herein "cryogenic" temperature or temperatures for "cryogenesis" or similar refer to a temperature at which a biological sample is exposed to freezing conditions. It will be understood in some aspects that the cryogenic temperature may include a freezing temperature of the biological sample and/or vitrification medium. It should further be understood that a cryogenic temperature is not bound by a particular threshold or range of values of temperatures in either Fahrenheit or Celsius, but instead can be determined by the relationship between temperature, pressure and molecular energy for the vitrification mixture of interest. It is further to be understood that as used herein, while certainly possible within the definition as set forth, "cryogenesis" and similar derivatives thereof are not limited to temperatures associated with liquid nitrogen at 1 atm or of about −80° C.

"Above cryogenic temperature," as used herein, accordingly refers to a temperature above the freezing point of a vitrification mixture. A point "above cryogenic temperature" may further include temperature values wherein relation to the surrounding atmosphere and the molecular energy, a freezing condition is absent. Room temperature, as used herein, refers to a temperature of about 25° C.

"Cryopreservation" typically refers to rapid cooling of a biological sample, often through the use of liquid nitrogen due to its low temperature which will rapidly cool a liquid material, or small volume of biological materials by direct immersion. The rate of cooling reduces the mobility of the material's molecules before they can pack into a more thermodynamically favorable crystalline state. Over a more prolonged period, the molecules can arrange to crystallize which can produce damaging results, particularly in biological samples. Water is a significant concern in biological samples as it can crystallize quickly, and its abundance in living tissues can prove to be significantly damaging the more that it is allowed to crystallize. Protective additives, often referred to as cryoprotectants, that interfere with the primary constituent's ability to crystallize may produce amorphous/vitrified material.

As used herein, "boiling" may refer to a point at which a material transitions to a vapor, often marked by the formation of vapor bubbles within the material that can escape into a surround atmosphere and dissipate therein.

"Glass transition temperature" means the temperature above which material behaves like liquid and below which material behaves in a manner similar to that of a solid phase and enters into amorphous/glassy state. This is not a fixed point in temperature, but is instead variable dependent on characteristics of the vitrification mixture of interest. In some aspects, glassy state may refer to the state the vitrification mixture enters upon dropping below its glass transition temperature.

"Amorphous" or "glass" refers to a non-crystalline material in which there is no long-range order of the positions of the atoms referring to an order parameter of 0.3 or less. Solidification of a vitreous solid occurs at the glass transition temperature $T_g$. In some aspects, the vitrification medium may be an amorphous material.

"Crystal" means a three-dimensional atomic, ionic, or molecular structure consisting of one specific orderly geometrical array, periodically repeated and termed lattice or unit cell.

"Crystalline" means that form of a substance that is comprised of constituents arranged in an ordered structure at the atomic level, as opposed to glassy or amorphous. Solidification of a crystalline solid occurs at the crystallization temperature $T_c$.

In some aspects, the present disclosure concerns methods to provide prolonged stability and/or storage of lipid particles, lipid particles housing one or more biological agents, mRNA, mRNA compositions and/or mRNA vaccine compositions. In this disclosure, an mRNA may be interchangeably used with an mRNA composition that includes mRNA and at least one additional molecule, or an mRNA vaccine that is an mRNA or mRNA composition suitable for administration to an organism or cell for induction of an immune response. In certain aspects, the storage can include temperatures of from around −80° C. to around 60° C. In some aspects, the mRNA can be stored in room temperature of around 25° C. to around 60° C., either for a prolonged or infinite period of time or transiently. During such storage, the mRNA is able to retain both structural integrity and physical activity or capability of such. In some aspects, the present disclosure concerns methods of preparing and storing mRNA so that the storage temperature is largely irrelevant, particularly with regard to retaining the activity and integrity of the mRNA.

In some aspects, the present disclosure concerns methods for stabilizing, storing and/or preserving mRNA or mRNA compositions such as mRNA vaccine compositions prior to its introduction into a cell or organism and/or incubation with a cell. In other aspects, the present disclosure concerns methods for storing and/or preserving an mRNA or mRNA vaccine compositions prior to administration to a subject, such as including the mRNA or mRNA vaccine composition in an injectable composition and/or a systemically administered composition.

mRNA and mRNA Compositions

In some aspects, the methods of the present disclosure concern stabilizing, storing and/or preserving mRNA or mRNA compositions. In some aspects, the methods can be initiated by obtaining an mRNA or mRNA composition or by isolating an mRNA to be stored and/or preserved. In some aspects, the mRNA or mRNA composition to be stored and/or preserved can initially be in a solution, such as an aqueous solution. In some aspects, the aqueous solution may be water. In other aspects, an aqueous solution may be predominantly water with added salts and/or buffers therein to promote the stability of the mRNA therein.

In some aspects, the methods include providing an mRNA or an mRNA composition or an mRNA vaccine composition to a capillary surface. An mRNA or an mRNA composition or an mRNA vaccine composition may, in some aspects, include a synthetic or a recombinant mRNA nucleic acid featuring a segment of interest intended to be translated in a cell (see, e.g. Rhodes (ed.) Synthetic mRNA: Production, Introduction Into Cells, and Physiological Consequences, Humana Press, 2016). In some aspects, the mRNA molecules may be prepared by in vitro transcription (IVT) or by transcription of a plasmid DNA (pDNA) construct.

In some aspects, the mRNA and/or mRNA composition is a purified mRNA molecule or purified mRNA composition. In certain aspects the mRNA can be purified by chromatographic methods, including reverse-phase fast-protein liquid chromatography or high-performance liquid chromatography. Further purification means can include binding and elution through the use of the polyA tail with an immobilized polyT or polyU.

In some aspects, the mRNA molecules may be nucleoside modified through the incorporation of modified bases, such as pseudouridine, 1-methylpseudouridine, 5-methylcytidine, N6-methyl adenosine, 2-thio-uridine, and 5-methoxyuridine.

In some aspects, the mRNA is capped. In some instances, the mRNA molecule or single strand is capped by a N7-methylated guanosine linked to the first nucleotide of the mRNA through a reverse 5'-5' triphosphate linker or by binding N7-methylated GTP. In some instances, the first nucleotide of the mRNA is 2'O methylated. In some aspects, the mRNA is capped with a synthetic or analog cap, such as an anti-reverse cap analog or a GpppG analog. In further aspects, the mRNA is capped with the cap, cap1, and/or cap2 structures known in the art. In some aspects, the mRNA cap is applied after transcription through the use of a vaccinia virus capping enzyme. In other aspects, the mRNA features a segment of interest, a UTR and/or a polyA tail.

In some aspects, an mRNA composition and/or an mRNA vaccine composition may include a packaged and/or encapsulated mRNA molecule or single strand, such as a lipid encapsulated mRNA. In some aspects, the mRNA may be encapsulated in an ionizable lipid. In some aspects, the mRNA composition may include lipid nanoparticles (LNPs) or lipid-like nanoparticles (LLNs) that contain at least one mRNA molecule or strand therein. In some aspects, the mRNA may be encapsulated in an LNP or LLN of two or more lipids, such as three, four, five or more.

In some aspects, the mRNA is encapsulated in an LNP. An LNP may include an ionic lipid (usually marked by three sections of an amine head, a linker and a hydrophobic tail, e.g. heptatriaconta-6,9,28,31-tetraen-19-yl 4-(dimethylamino)butanoate (DLin-MC3-DMA or MC3), DLinDMA, and DLin-KC2-DMA). In some aspects, the LNP may include an ionic lipid, a polyethylene glycol and a cholesterol. In further aspects, the LNP may include a combination of an ionic lipid with polyethylene glycol (PEG), cholesterol and/or distearoyl phosphocholine (see, e.g., Sabnis et al., *Mol. Ther.* 26: 1509-1519 (2018); Pardi et al. *J. Exp. Med.* 215:1571-1588 (2018); and, Pardi et al. *J. Control. Release* 217: 345-351 (2015)). In some aspects, an LNP includes, but is not limited to (4-hydroxybutyl) azanediyl)bis (hexane-6,1-diyl)bis(2-hexyldecanoate), 2-[(polyethylene glycol)-2000]-N,N ditetradecylacetamide, Distearoyl-sn-glycero-3-phosphocholine (DPSC), and cholesterol. In some aspects, and LNP includes (heptadecan-9-yl 8-((2-hydroxyethyl) (6-oxo-6-(undecyloxy) hexyl) amino) octanoate), 1-monomethoxypolyethyleneglycol-2,3-dimyristoylglycerol with polyethylene glycol of average molecular weight 2000, 1,2-Distearoyl-sn-glycero-3 phosphocholine, and cholesterol. Optionally, and LNP is as provided in Schoenmaker, et al., *International Journal of Pharmaceutics*, Volume 601, 2021, 120586.

In some aspects, the LNP may further include a "helper" lipid. A helper lipid may include 1,2-dioleoyl-3-trimethylammoniumpropane (DOTAP) and/or dioleoylphosphatidylethanolamine (DOPE) and/or lipofectamine and/or dioleoylphosphatidylcholine (DOPC) and/or phosphatidylethanolamine (dioleoyl PE) and/or 3β-[N—(N', N'-dimethylaminoethane)-carbamoyl]-cholesterol (DC-Chol) (see, e.g., Du et al. *Scientific Reports* 4: 7107 (2014) and Cheng et al. *Advanced Drug Delivery Reviews* 99(A): 129-137 (2016)).

In some aspects, the mRNA composition and/or an mRNA vaccine composition may include a vehicle for improving cellular uptake of the mRNA therein, such as a polymer or a polymer modified with fatty chains or a polymethacrylate with amine-bearing side chains or a polyaspartamide with oligoaminoethylene side chains or a poly(beta-amino) ester (PBAE). In some aspects, the vehicle of the mRNA composition may include a dendrimer, such as a polyamidoamine or a polypropylenimine based dendrimer.

In some aspects, an mRNA composition and/or an mRNA vaccine composition may include a cell-penetrating peptide (CPP) or a carrier protein to assist as a vector for mRNA delivery to a cell, including a CPP with arginine-rich amphipathic RALA sequence repeats or a protamine or a D-isomeric Xentry-protamine. In further aspects, the mRNA composition may include a zwitterionic lipid (ZAL) or a combination of cationic and zwitterionic lipids. An overview of current delivery vehicles for mRNA is set forth by Kowalski et al. (Mol. Ther. 27(4): 710-728 (2019)). Examples of carrier proteins include tetanus toxoid (TT), diphtheria toxoid (DT), CRM197 (a DT variant from *C. dipthereriae* C7), a meningococcal outer membrane protein complex (OMPC), *H. influenza* protein D, and keyhole limpet hemocyanin (KLH).

In some aspects, the present disclosure concerns an mRNA composition for an mRNA vaccine composition. In some aspects, the mRNA molecule therein contains a segment of interest to express an exogenous protein or fragment thereof or a designed antigen, whereby expressing of the segment of interest allows the cell translating such to process and/or present the expressed segment of interest or fragment thereof to the immune cells and systems of the cell's host organism. In some aspects, an mRNA is a nucleoside modified mRNA such that some nucleosides are replaced with other naturally occurring nucleosides or by synthetic nucleoside analogues, optionally to increase immunogenicity relative to an unmodified mRNA. Examples of COVID-19 vaccines using modRNA include those developed by the cooperation of BioNTech/Pfizer/Fosun International (BNT162b2), and by Moderna (mRNA-1273) illustratively as described in Krammer F, *Nature,* 2020; 586 (7830): 516-527 or Dolgin, E. *Nature Biotechnology,* 2020: d41587-020-00022-y. doi:10.1038/d41587-020-00022-y.

A segment of interest is optionally any segment that encodes a desired protein. In some aspects a segment of interest encodes a portion of the SARS-CoV-2 virus, influenza virus, or other viral or bacterial antigens. Illustrative proteins encoded by a segment of interest include, for example, SARS-CoV-2 spike (S) protein and SARS-CoV-2 nucleocapsid (N) protein. N and S proteins of SARS-CoV-2 are known by sequence and are commercially available through various vendors, including for example RayBiotech (Peachtree Corners, VA). A segment of interest may be a portion of a viral antigen that is normally exposed to the environment outside the viral capsid. For example, in aspects, the segment of interest may encode the S1 or S2 subunit of the SARS-CoV-2 spike protein S. However, the skilled artisan will appreciate that other peptides or fragments thereof may be similarly encoded, optionally any such exposed protein or protein portion on the extracellular side of the capsid or membrane of any infectious agent. The SARS-CoV-2 spike protein has been characterized by Ou, et al., *Characterization of spike glycoprotein of SARS-CoV-2 on virus entry and its immune cross-reactivity with SARS-CoV, Nature Communications,* 11, article 1620 (2020); and Ibrahim, et al., *COVID-19 spike-host cell receptor* 15 *GFP78 binding site prediction, J. Infect., S*0163-4453(20) (Mar. 10, 2020), each of which is incorporated herein by reference in its entirety.

In some aspects, the mRNA composition and/or an mRNA vaccine composition may include an mRNA molecule that includes more than one segment of interest. As is understood, an mRNA vaccine composition can provide for both an expressed antigen and for viral replication machinery to allow the molecules to self-amplify or such necessary modifications to ensure that viral replication is suppressed or eliminated. In certain aspects, the mRNA or mRNA composition may include, either as separate mRNA strands or included within a single strand, segments of interest that encode for viral replication machinery, such as utilizing a viral RNA genome with the antigenic segment of interest replacing structural proteins to provide additional RNA complexing agents (see, e.g., Geall et al. *Proc. Natal. Acad. Sci. USA* 109: 14606-14609 (2012) and Pardi et al., *Nat. Rev. Drug Discov.* 117:261-279 (2018)). In some aspects, the mRNA vaccine composition may be part of a viral vector, wherein the viral vector is a modified viral genome that is designed to be non-pathogenic and allow for a host cell to transcribe the segment of interest and/or the mRNA in vivo. Examples of viral vectors include modified versions of a retrovirus, a lentivirus, an adenovirus, a vaccinia virus, an adeno-associated virus and a cytomegalovirus (see, e.g., Ura et al., *Vaccines* 2: 624-641 (2014)).

In some aspects, the mRNA is an mRNA vaccine composition. In some aspects, the mRNA vaccine composition includes mRNA molecule(s) encapsulated in a lipid or lipid-like nanoparticle. Such nanoparticles may optionally include an ionic lipid, a cholesterol (or optionally absent cholesterol), a polyethylene glycol and/or a helper lipid, such as DOTAP, DOPE, DOPC and/or dioleoyl PE.

An mRNA vaccine composition may include a naked mRNA molecule, an mRNA and a protamine, an mRNA in a cationic nanoemulsion, an mRNA in an LNP, an mRNA in a dendrimer nanoparticle, an mRNA and protamine in a liposome or LNP, an mRNA in a cationic polymer (e.g. polyethylenimine), an mRNA in a cation polymer liposome, an mRNA and a polysaccharide, an mRNA in a cationic lipid nanoparticle (e.g. 1,2-dioleoyloxy-3-trimethylammonium-propane or dioleoylphosphatidylethanolamine), mRNA in a cationic lipid and cholesterol nanoparticle, and mRNA in a cationic lipid, cholesterol and poly-ethylene glycol (PEG) nanoparticle.

In some aspects, the mRNA vaccine composition can include ex vivo mRNA loaded dendritic cells. In such aspects, typically a dendritic cell from the subject to be immunized is obtained and the mRNA introduced therein for later replacement back into the host subject. As dendritic cells are potent antigen-present cells, the ex vivo mRNA loading provides a mechanism to potently recruit the immune system when re-introduced. In such aspects, the dendritic cell itself can be vitrified by the methods disclosed herein either pre or post mRNA introduction. In other aspects, a dendritic cell can uptake a reconstituted mRNA as set forth herein.

In further aspects, the mRNA, mRNA compositions and/or mRNA vaccine compositions may further include an adjuvant. As set forth herein in some aspects, the mRNA can be added to a further composition, such as adding an mRNA to a lipid mixture to encase the mRNA in an LNP. In other aspects, the mRNA can be stored as provided herein, reconstituted and an adjuvant added. In further aspects, an adjuvant can be mixed or included with the mRNA or mRNA composition prior to vitrification. Adjuvants may include aluminum based (e.g. aluminum salts) compounds such as aluminum hydroxyphosphate sulfate, aluminum hydroxide, aluminum phosphate, and potassium aluminum sulfate. Adjuvants may further include AS04 (monophosphoryl lipid A and aluminum salt), MF59 (oil in water emulsion including squalene), AS01B (monophosphoryl lipid A and QS-21 (from Chilean soapbark tree) in a liposomal formulation), and CpG 1018 (cytosine phosphoguanine synthetic DNA) and TLR agonists. Further adjuvants may include the presence of other mRNAs encoding CD70, CD40L and TLR4 (optionally constitutively active) to allow for better cell intake of the mRNA and/or cellular expression of the segment of interest.

Vitrification Mixture

In some aspects, the present disclosure concerns placing a lipid particle, lipid particle housing one or more cargo molecules, mRNA, mRNA composition, or mRNA vaccine composition within a vitrification mixture on a capillary or a capillary bed. The mRNA may be a naked mRNA, an mRNA composition or an mRNA vaccine composition as set forth herein. The mRNA may further be part of a vitrification mixture placed on a capillary or a capillary bed. A vitrification mixture may include the lipid particle, lipid particle housing one or more cargo molecules, mRNA, mRNA composition, or mRNA vaccine composition, and a vitrification medium. In further aspects, a vitrification medium may be added to a capillary bed, followed by addition of a lipid particle, lipid particle housing one or more cargo molecules, mRNA, mRNA composition, or mRNA vaccine composition thereto to provide a vitrification mixture on a capillary bed. It will be appreciated in the art that all components likely or possibly to come into contact with an mRNA molecule as set forth herein be prepared and/or treated to be free or substantially free of degradative enzymes to the mRNA, including any potential or likely source of RNAse.

A vitrification medium can include a glass forming agent. The identification of glass forming agents have opened opportunities for successful preservation of biological molecules, cells or tissues. In the presence of appropriate glass forming agents, it is possible to store biological materials in a vitrified matrix above cryogenic temperatures with vitrification achieved by dehydration as provided herein. The ability to survive in a dry state (anhydrobiosis) depends on several complex intracellular physiochemical and genetic mechanisms. Among these mechanisms is the intracellular accumulation of sugars (e.g., saccharides, disaccharides, oligosaccharides) that act as a protectant during desiccation. Trehalose is one example of a disaccharide naturally produced in desiccation tolerant organisms. Pullulan is an example of a polysaccharide similarly suited to application in desiccation. Sugars like trehalose and pullulan may offer protection in several different ways. A trehalose molecule may effectively replace a hydrogen-bounded water molecule from the surface of a molecule without changing its conformational geometry and folding due to the unique placement of the hydroxyl groups on a trehalose molecule. Furthermore, many sugars have a high glass transition temperature, allowing them to form glass at above cryogenic temperature or a room temperature glass at low water content. The highly viscous 'glassy' state reduces the molecular mobility, which in turn prevents degradative biochemical reactions that lead to deterioration of function.

The presence of appropriate vitrification agents in a vitrification medium can be essential as the lipid particle, lipid particle housing one or more cargo molecules, mRNA, mRNA composition, or mRNA vaccine composition desiccates under the surrounding conditions as set forth herein. Fast desiccation methods by itself does not necessarily assure success in the viability of the cells or other vitrified biological material following desiccation absent other considerations as provided herein. A vitrification medium that forms glass and/or that suppresses the formation of crystals in other materials may be required. A vitrification medium may also provide osmotic protection or otherwise enable cell survival during dehydration of the mRNA or compositions thereof. Illustrative examples of agents to include in a vitrification medium may include one or more of the following: dimethylsulfoxide, glycerol, sugars (e.g disaccharides, e.g. trehalose), polyalcohols, methylamines, betines, antifreeze proteins, synthetic anti-nucleating agents, polyvinyl alcohol, cyclohexanetriols, cyclohexanediols, inorganic salts, organic salts, ionic liquids, or combinations thereof. In some aspects, a vitrification medium optionally contains 1, 2, 3, 4, or more vitrification agents.

In some aspects, a vitrification medium may include a vitrification agent at a concentration that is dependent on the identity of the vitrification agent. Optionally, the concentration of the vitrification agent is at a concentration that is below that which will be toxic to the mRNA or compositions thereof being vitrified where toxic is such that functional or biological viability is not achieved upon subsequent sample use. The concentration of a vitrification agent is optionally of about 500 micromolar (μM) to about 6 molar (M), or any value or range therebetween, including about 1, 2, 3, 4, or 5 M. For the vitrification agent trehalose, the concentration is optionally of about 1 M to about 6 M, including 2, 3, 4, or 5 M. Optionally, the total concentration of all vitrification agents when combined is optionally of about 1M to about 6M, including 2, 3, 4, or 5 M Trehalose, a glass forming sugar, has been employed in anhydrous vitrification and may provide desiccation tolerance in several ways. However, vitrified 1.8 M trehalose in water has a glass transition temperature of −15.43° C. To achieve vitrification above 0° C., higher concentrations (6-8 M) are required which could be damaging to the mRNA or compositions thereof. Alternatively, the vitrification medium may include buffering agents and/or salts to increase the Tg value of the VM. In some aspects, a vitrification medium may optionally include water or a solvent and/or a buffering agent and/or one or more salts and/or other components. A buffering agent may be any agent with a pKa of about 6 to about 8.5 at 25° C. Illustrative examples of buffering agents may include HEPES, TRIS, PIPES, MOPS, among others. A buffering agent may be provided at a concentration suitable to stabilize the pH of the vitrification medium to a desired level.

A vitrified medium including 1.8 M trehalose, 20 millimolar (mM) HEPES, 120 mM ChCl, and 60 mM Betine provides a glass transition temperature of +9° C. An exemplary vitrification medium for the capillary assisted vitrification method disclosed herein may include trehalose, and one or more buffering agents containing large organic ions (>120 kDa) such as choline or betine or HEPES as well as buffering agent(s) containing small ions such as K or Na or Cl. In some aspects, the vitrification medium may include trehalose, glycerol and phosphate-buffered saline. The vitrification medium may further be sterilized, such as through heat treatment or by filtration such as through a 0.2 μm membrane filer. In further aspects, the vitrification medium may be mixed with a volume of the mRNA, mRNA composition or mRNA composition. In some aspects, the vitrification medium is mixed with the mRNA, mRNA composition or rRNA composition at a ratio of about 10;1, 9:1, 8:1, 7:1, 6:1, 5:1, 5:1, 3:1, 2:1, 1:1, 1:2, 1:3, 1:4, 1:5, 1:6, 1:7, 1:8, 1:9, or 1:10.

Pressure and Heat

In some aspects, the vitrification mixture of the lipid particle, lipid particle housing one or more cargo molecules, mRNA, mRNA composition, or mRNA vaccine composition and the vitrification medium is placed on a capillary network or a contiguous capillary network to enhance evaporation of the vitrification medium and any fluids within the mRNA. In some aspects, the methods of the present disclosure concern applying a low atmospheric pressure to the vitrification mixture on the capillary network. In some aspects, a low pressure is applied while further providing heat to avoid the VM from crystallizing or freezing. The present disclosure provides for a vitrification process that combines low atmospheric pressure and heat energy, optionally heat energy from a particular direction or location relative to the membrane, to achieve rapid vitrification of the mRNA in a vitrification mixture. In some aspects, the present disclosure concerns application of heat energy to a vitrification mixture as vitrification occurs under reduced atmospheric pressure. In some aspects, heat energy is applied to a vitrification mixture to prevent the crystallization of the vitrification mixture or contents therein, such as the mRNA or mRNA composition.

In some aspects, the present disclosure concerns vitrification of a lipid particle, lipid particle housing one or more cargo molecules, mRNA, mRNA composition, or mRNA vaccine composition in low atmospheric pressure. In some aspects, the desiccation may occur in a desiccation chamber, whereby the vitrification mixture may be placed therein so as to be exposed to low atmospheric pressure. Such a desiccation chamber may be connected to a vacuum source to apply a low atmospheric pressure to the lipid particle, lipid particle housing one or more cargo molecules, mRNA, mRNA composition, or mRNA vaccine composition. As set forth herein, a vitrification mixture can be prepared with a vitrification medium or a cryopreservative such as trehalose and subjected to low atmospheric pressure, such as through application of a vacuum. In some aspects, the low atmospheric pressure is from about 0.9 atmospheres (atm) to about 0.005 atm, including 0.85, 0.8, 0.75, 0.7, 0.65, 0.6, 0.55, 0.5, 0.45, 0.4, 0.35, 0.3, 0.255, 0.25, 0245, 0.24, 0.235, 0.23, 0.225, 0.22, 0.215, 0.21, 0.205, 0.2, 0.195, 0.19, 0.185, 0.18, 0.175, 0.17, 0.165, 0.16, 0.155, 0.15, 0.145, 0.14, 0.135, 0.13, 0.125, 0.12, 0.115, 0.11, 0.105, 0.1, 0.095, 0.09, 0.085, 0.08, 0.075, 0.07, 0.065, 0.06, 0.055, 0.05, 0.045, 0.04, 0.035, 0.03, 0.025, 0.02, 0.015, and 0.01 atm.

In other aspects, the pressure within the desiccation chamber is lowered to a point above the triple point of the vitrification mixture. In other aspects, the pressure is lowered to a point above the triple point of water, such as greater than 0.006 atm. As set forth herein, lowered atmospheric pressure lowers the temperature of the vitrification mixture while also reducing its boiling point. In some aspects the pressure within the desiccation chamber is lowered to about 0.04 atm or about 29 mmHg.

In further aspects, the temperature of the vitrification mixture is controlled during desiccation and/or vitrification. For example, a vitrification mixture is placed within a desiccation chamber and heat energy is applied to the vitrification mixture to restrict or prevent the vitrification mixture from experiencing a cryogenic temperature. In some aspects, heat energy is transferred to the vitrification mixture to prevent crystallization therein.

In some aspects, the temperature of the lipid particle, lipid particle housing one or more cargo molecules, mRNA, mRNA composition, or mRNA vaccine composition is controlled within an applied vacuum or reduction in atmospheric pressure around the vitrification mixture, optionally to within 30 degrees C. from the Tc, optionally within 20 degrees C. from the Tc, optionally within 10 degrees C. from the Tc, optionally within 5 degrees C. from the Tc, optionally within 4 degrees C. from the Tc, optionally within 3 degrees C. from the Tc, optionally within 2 degrees C. from the Tc, optionally within degrees C. from the Tc, optionally within less than 1 degrees C. from the Tc. As is discussed herein, application of a low atmospheric pressure can significantly lower the temperature of the vitrification mixture causing the vitrification mixture to crystallize. If the mRNA or the surrounding media crystallizes, irrevocable damage can occur therein that can negatively impact any desired activity or use when reconstituted. As is also identified herein, reduction in atmospheric pressure around the vitrification mixture can alter the molecular activity within the vitrification mixture, such that the boiling point is reduced. Similar to cryogenesis, boiling the mRNA and/or vitrification medium or overheating can be detrimental. Boiling of a vitrification mixture can lead to loss of tertiary structure, crosslinking and degradation of the mRNA components therein, rendering any activity upon reconstitution compromised. In certain aspects, the process of the present disclosure concerns maintaining a vitrification mixture at a temperature above a cryogenic temperature while in low atmospheric pressure such as a vacuum, partial vacuum or in a generally reduced pressure atmosphere.

In certain aspects, the vitrification mixture including the lipid particle, lipid particle housing one or more cargo molecules, mRNA, mRNA composition, or mRNA vaccine composition and the vitrification medium may be heated directly to control the temperature of such during desiccation. In other aspects, the vitrification mixture including the lipid particle, lipid particle housing one or more cargo molecules, mRNA, mRNA composition, or mRNA vaccine composition and the vitrification medium may have the temperature of such controlled by conduction, convection and/or radiation means. In other aspects, the vitrification mixture including the lipid particle, lipid particle housing one or more cargo molecules, mRNA, mRNA composition, or mRNA vaccine composition and the vitrification medium may have its temperature controlled by controlling the temperature outside of the desiccation chamber and relying on conduction through the desiccation chamber or portion thereof to control the temperature of the vitrification mixture. In such instances, it will be appreciated that the physical properties of the walls of the desiccation chamber may need to be taken into consideration. For example, a poorly conducting material of the desiccation chamber may require an applied temperature different from that required by the vitrification mixture in order to allow for the vitrification mixture to receive the appropriate heat energy. Such necessary adaptations will be readily appreciated by those in the art. In some aspects, heat may be applied through a heating pad, a heated bath, a flame, a heated bed, such as glass bead, a heated block and similar. In some cases the heat energy may be from an electric source of generated heat and/or a heat energy released by combustion and/or a heat energy generated by electrical resistance.

In some aspects, heat energy can be provided to the vitrification mixture through an underlying support substrate. While a porous material of a contiguous capillary network may also provide heat energy to the vitrification mixture, in some instances the porous material is of a poor conducting material, such as glass or a polymer. However, the underlying substrate may be of a metal or similarly efficient conducting material and easily connected to a heat source outside of the desiccation chamber or an electrical source and provide heat by resistance created therein. The application of heat energy from the solid support may further provide a temperature gradient to assist in capillary evaporation.

A heat energy may be applied from a desired direction. It was found that application of heat from below or within a capillary channel or membrane such that the heat is targeted to the bulk of the liquid itself may, in some aspects, be detrimental by causing film boiling in the material prior to achieving a glassy form. Alternatively, heat applied from a direction above a meniscus formed by the end of a capillary channel promotes vitrification without causing boiling of the liquid alone or during exposure to reduced atmospheric pressure. A direction above a meniscus may be at both ends of a capillary channel such as when a channel or membrane is loaded with vitrification mixture and subjected to heating and reduction in atmospheric pressure to promote vitrification of the material. By allowing a space (gas filled or vacuum) without liquid between the heat source and end of a capillary channel or vitrification membrane surface, improved vitrification is achieved thereby allowing improved biological activity stability of the mRNA.

In some aspects, the vitrification mixture including the lipid particle, lipid particle housing one or more cargo molecules, mRNA, mRNA composition, or mRNA vaccine composition and the vitrification medium is maintained at a temperature above its cryogenic temperature during vitrification under low atmospheric pressure. In some aspects, the vitrification mixture is preheated prior to desiccation under low atmospheric pressure. In other aspects, the vitrification mixture is heated during vitrification under low atmospheric pressure. In other aspects, heat is applied at or around the time vitrification commences. It will be appreciated that the amount of heat energy applied to the vitrification mixture may be constant or may vary during vitrification under low atmospheric pressure process. In some aspects, the introduction of low atmospheric pressure within the desiccation chamber can cause a rapid drop in temperature of the vitrification mixture. In such aspects, having the vitrification mixture ready to receive or already receiving heat energy can increase the recovery rate from the drop in temperature (see, e.g., FIG. 5).

In certain aspects, a constant temperature is applied to the vitrification mixture, such that the vitrification mixture is maintained at a temperature of from about $T_g$ of the vitrification mixture in ° C. to about 40° C., including about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, and 39° C. In certain aspects, a higher temperature may be applied to the desiccation chamber or the porous material to provide the necessary heat energy to the vitrification mixture. Such applied temperatures may be of from about 15° C. to about 70° C., depending on the size of the desiccation chamber and the conductive means available to transfer effectively to the lipid particle, lipid particle housing one or more cargo molecules, mRNA, mRNA composition, mRNA vaccine composition and/or vitrification medium.

In some aspects of the present disclosure, the vitrification mixture is placed in a vacuum or partial vacuum at an elevated temperature or maintained at a temperature above the cryogenic temperature of the vitrification mixture at the atmospheric pressure applied, such that the vitrification mixture does not experience cryogenic temperature during the rapid decrease in atmospheric pressure. In further aspects, the temperature of the vitrification mixture will fall below the $T_g$ of the vitrification medium to allow the vitrification of the mRNA or compositions thereof.

In some instances, maintaining the low atmospheric pressure can require containing the vitrification mixture in a sealed enclosure, such as a desiccation chamber. It will be appreciated by those skilled in the art that providing and/or maintaining a low atmospheric pressure around the vitrification mixture will typically require that the desiccation chamber be capable of withstanding the low pressure therein. Such can be of any suitable or desired shape and/or material, being constrained by a requirement to maintain a low atmospheric pressure therein, requiring a sufficient seal and sufficient wall strength. The desiccation chamber can be operably connected to a vacuum source to lower the atmospheric pressure therein, while further allowing air to return upon vitrification completion. The desiccation chamber may be sufficiently sealed or closed so as to allow for an applied vacuum to effectively lower the atmospheric pressure in the desiccation chamber to the desired range.

Capillary-Assisted Evaporation

In further aspects, a capillary network can prevent the vitrification mixture from boiling under a reduced atmospheric pressure. The principles of capillary assisted evaporation and devices that may be used for vitrification may be as described in U.S. Pat. No. 10,568,318, which is incorporated by reference in its entirety herein. In some aspects, a heat energy may be applied to a vitrification mixture as it undergoes desiccation and vitrification on a capillary network. In some aspects, an underlying capillary network can allow for even and complete vitrification and desiccation of a vitrification mixture receiving heat energy while protecting the vitrification mixture from boiling. The capillary network can be a contiguous network of capillaries. In some instances, the capillary network can be provided by an underlying porous material, such as a membrane, or an underlying contoured or ridged surface wherein the troughs and apices thereof provide a bed of capillaries.

The presence of the vitrification mixture over a capillary network allows for fast evaporation by drawing the vitrification mixture out with capillary action. The presence of a contiguous capillary network further allows the fluid volume of the vitrification medium to evenly evaporate and prevent boiling while also preventing excess fluid build-up over the mRNA or compositions thereof, which can also experience damaging boiling. Similarly, a porous material such as a membrane, may provide an underlying capillary network. In such aspects, a porous material, such as a membrane, is directly underlying the mRNA or compositions thereof and the capillary action therein provides for enhanced evaporation. Accordingly, in some aspects of the present disclosure, the vitrification mixture is placed on a contiguous capillary network. In further aspects, the vitrification mixture is placed on a patterned and/or ridged and/or contoured porous material of a contiguous capillary network. In further aspects, the contiguous capillary network is formed by patterns and/or ridges and/or contours within or on walls of a desiccation chamber. In other aspects, the capillary network is provided by a porous material.

Figure 1B:
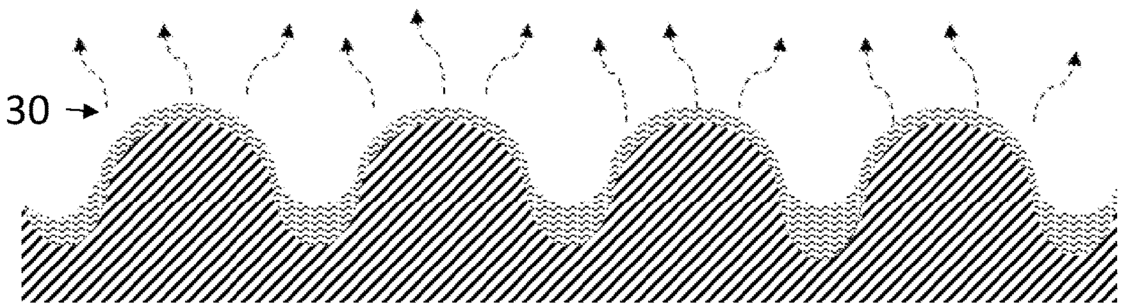
FIG. 1B shows a contoured capillary bed, wherein desiccation can preferentially occur at the peaks of the contours 30 where capillary phenomena from the troughs toward the peaks during desiccation can enhance overall vitrification rate and allow for vitrification of large sample volumes relative to FIG. 1A.
Figure 1C:
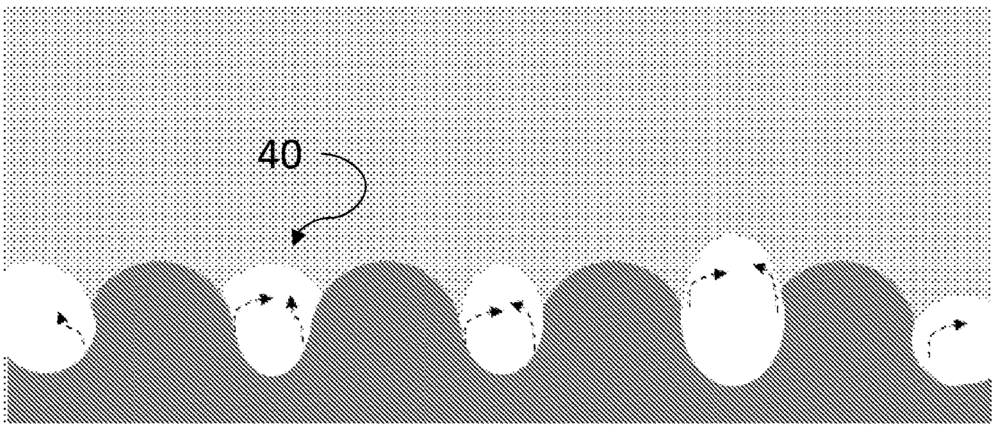
FIG. 1C shows liquid filling the surface patterns when there is excess fluid within the contoured capillaries 40, resulting in bubble nucleation and boiling becoming dominant under reduced pressure which may lead to damage of sensitive molecules.

With reference to FIG. 1A, depicted is a contiguous hydrophilic bed 10 covered by application of a thin liquid layer of vitrification mixture 20. Prevention of boiling under reduced atmosphere can be avoided and/or reduced with an extremely thin liquid film on a hydrophilic surface as shown in FIG. 1A. However, while prevention of boiling is possible, the available surface area reduces the amount of liquid that can be vitrified. The presence of a contoured surface, such as that set forth in FIG. 1B, effectively provides a surface upon which the vitrification mixture can be subjected to a capillary action due to preferential desiccation occurring at the peaks thereby drawing moisture up from the troughs during the vitrification process and that can similarly protect the mRNA or compositions thereof from boiling. Further, as the sample vitrifies at the peaks of the contours, capillary action draws fluid from the underlying trough, thereby promoting excellent vitrification of the vitrification mixture. Similarly, if a porous material of a membrane of capillaries supports the mRNA or compositions thereof, capillary action will draw fluid from the capillary channels when the vitrification mixture is placed thereon and provide even and complete vitrification and desiccation of the mRNA or compositions thereof. However, as set forth in FIG. 1C, if the capillary action cannot successfully draw fluid up, such as in the case of a fluid loading that is too great, the liquid fills the surface patterns or is retained in the troughs, where bubble nucleation and boiling becomes dominant under reduced pressure which may lead to damage of sensitive molecules contained therein.

The capillary network formed from either an underlying patterned ridged support or of a porous material such as a membrane may be made of a material that is not toxic and not reactive to the mRNA or compositions thereof and does not react chemically or physically with the vitrification medium. The material can be of a suitable polymer, metal, ceramic, glass, or a combination thereof. In some aspects, a contiguous capillary network is formed from a material of polydimethylsiloxane (PDMS), polycarbonate, polyurethane, polyethersulphone (PES), polyester (e.g. polyethylene terephthalate), among others. Illustrative examples of a capillary channel containing membrane suitable as a surface in the devices and processes provided herein include hydrophilic filtration membranes such as those sold by EMD Millipore, Billerica, MA. In certain aspects, the porous material does not substantially bind, alter, or otherwise produce a chemical or physical association with a component of a mRNA or compositions thereof and/or vitrification medium. The porous material is optionally not derivitized. Optionally, capillary channels may be formed in a substrate (e.g. desiccation chamber walls) of desired material and thickness by PDMS formation techniques, laser drilling, or other bore forming technique as is known in the art.

Figure 4:
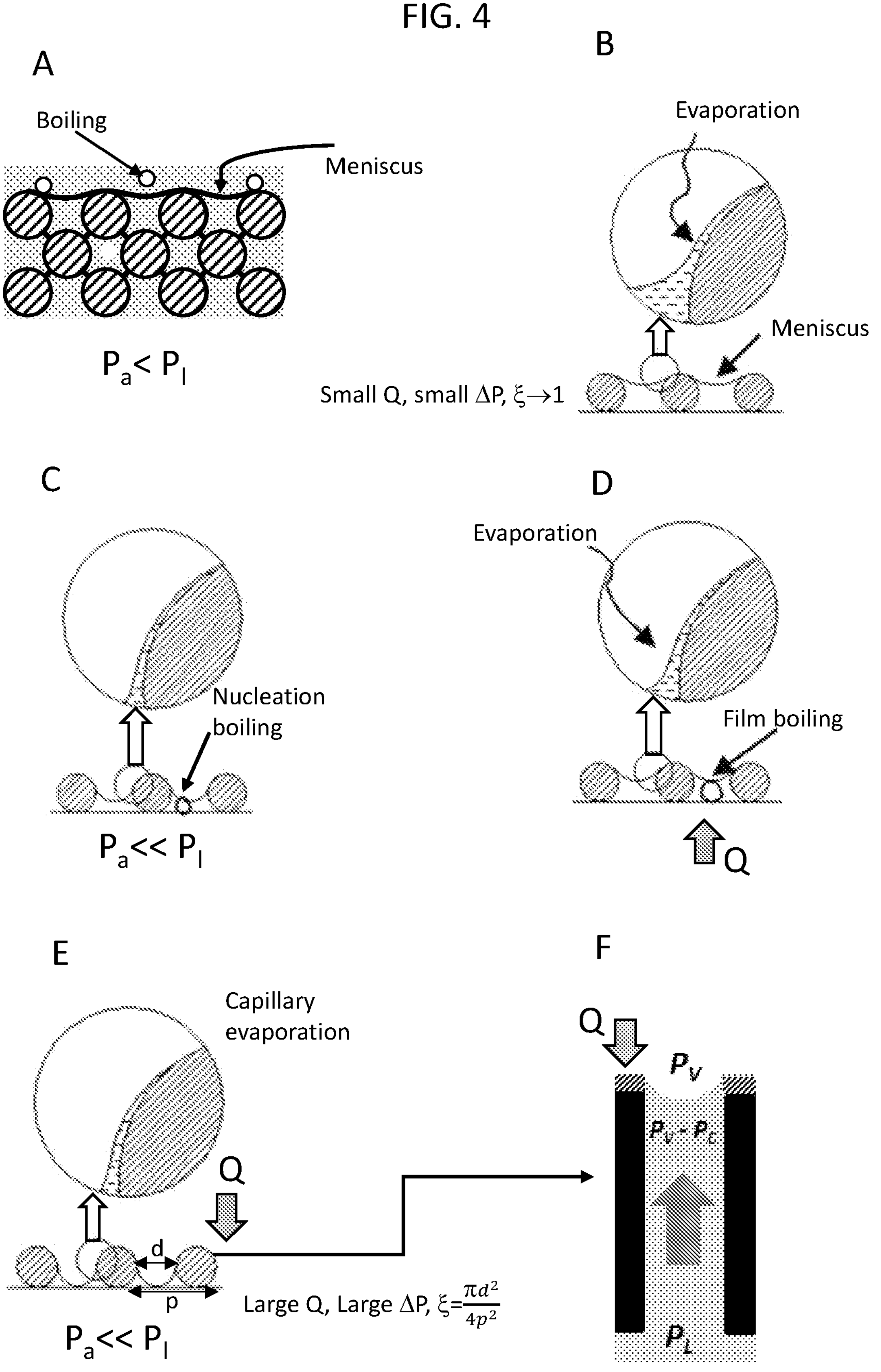
FIG. 4 at (A) shows that when excess liquid accumulates on the surface of the capillary membrane, the capillary effect is not realized such that under vacuum boiling still can occur in the accumulated liquid, which is undesirable. To realize the capillary effect the liquid may be accommodated within the pores of the membrane forming a meniscus. This localization on an undulating surface is similar and shaped by the peaks and troughs of the material. The liquid fraction (ξ) at the capillary interface, i.e., the area (in two dimensional schematic) occupied by liquid is one parameter that allows for optimization of capillary evaporation. Capillary driven evaporation occurs when the viscous pressure drop in the liquid surpasses the maximum capillary pressure at the liquid-vapor interface. The liquid fraction ξ is related to the overall pressure drop from the bulk to the liquid-vapor interface. Under atmospheric pressure and no applied heat flux (B) the liquid covers large area, leading to a liquid fraction, ξ→1. Under these conditions the capillary driven evaporation rate is minimal. Reducing the ambient pressure as shown in (C), reduces ξ and in turn increases the evaporation rate. However, beyond certain threshold pressure drop, nucleation boiling can occur which is undesirable. An applied heat flux Q as shown in (D) can also enhance the evaporation rate, but the risk of undesirable film boiling exists when the heat is applied from the supply side of the liquid to the capillary channel. Applying the heat flux from the surface of the capillary meniscus as shown in (E), significantly reduces the risk of film boiling. Large ΔP and Q applied in a counter gradient fashion as shown in (F), leads to the liquid meniscus confined to the pores, i.e., the liquid fraction ξ<<1 (e.g. ~0.25), resulting in highest evaporation rate while avoiding boiling. Therefore, maintaining a temperature gradient between the surface and the bulk liquid leads to capillary evaporation as illustrated in (F), where the fast evaporation can be achieved. As the liquid level recedes into the capillary membrane, capillary evaporation phenomena is still realized as long as the pressure gradient and temperature gradients are maintained.

In some aspects, the capillary network is of sufficient thickness to restrict liquid or fluid from accumulating on the surface thereof. To realize the capillary effect the liquid may be accommodated within the pores of the membrane forming a meniscus. The liquid fraction ($\xi$) at the capillary interface, i.e., the volume occupied by the liquid is a parameter for consideration to promote improved capillary evaporation. Capillary driven evaporation occurs when the viscous pressure drop in the liquid surpasses the maximum capillary pressure at the liquid-vapor interface. The liquid fraction $\xi$ is related to the overall pressure drop from the bulk to the liquid-vapor interface. Under atmospheric pressure and no applied heat flux (FIG. 4B) the liquid covers large fraction, leading to a liquid fraction, $\xi \rightarrow 1$. Under these conditions, the capillary driven evaporation rate is minimal. Reducing the ambient pressure as shown in FIG. 4C, reduces and in turn increases the evaporation rate. However, beyond certain threshold pressure drop, nucleation boiling can occur which is undesirable. An applied heat flux Q as shown in FIG. 4D can also enhance the evaporation rate, but the risk of film boiling exists, which is also undesirable. Applying the heat flux from the surface of the capillary meniscus as shown in FIG. 4E, eliminates or reduces the risk of film boiling. Under large $\Delta P$ and Q applied in a counter gradient fashion as shown in FIG. 4F, leads to the liquid meniscus confined to the pores, i.e., the liquid fraction $\xi \ll 1$ (~0.25), resulting in highest evaporation rate while avoiding boiling $$(\xi = \frac{\pi d^2}{4p^2},$$

where p is distance between ridges or height of the membrane and d the diameter of the circle formed by the shape of the liquid meniscus). Therefore, maintaining a temperature gradient between the surface and the bulk liquid leads to capillary evaporation as illustrated in FIG. 4F, where the fast evaporation can be achieved. As the liquid level recedes into the capillary membrane, capillary evaporation phenomena is still realized as long as the pressure gradient and temperature gradients are maintained. In some aspects, a capillary network under the mRNA or compositions thereof may assist in the evaporative processes during desiccation.

Figure 3:
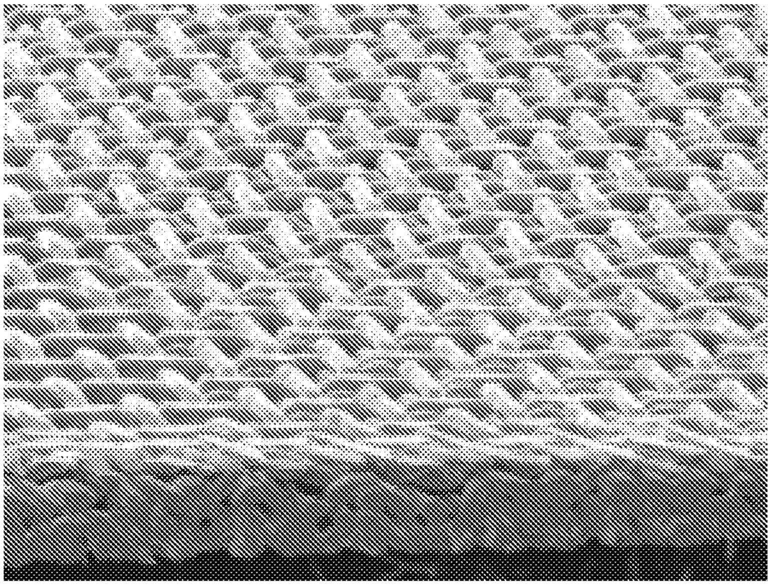
FIG. 3 shows an exemplary capillary membrane to facilitate fast desiccation of larger volume of liquid under vacuum to form a vitrified glassy material.
Figure 6A:
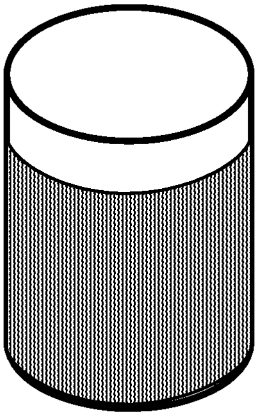
FIG. 6A illustrates one exemplary aspect of the present disclosure wherein the desiccation device itself features contoured walls. The desiccation device can be formed of a hydrophilic capillary membrane rolled into a cylindrical shape. The cylinder can house a vitrification medium within the membrane similar to FIG. 4 thereby promoting improved vitrification.
Figure 6B:
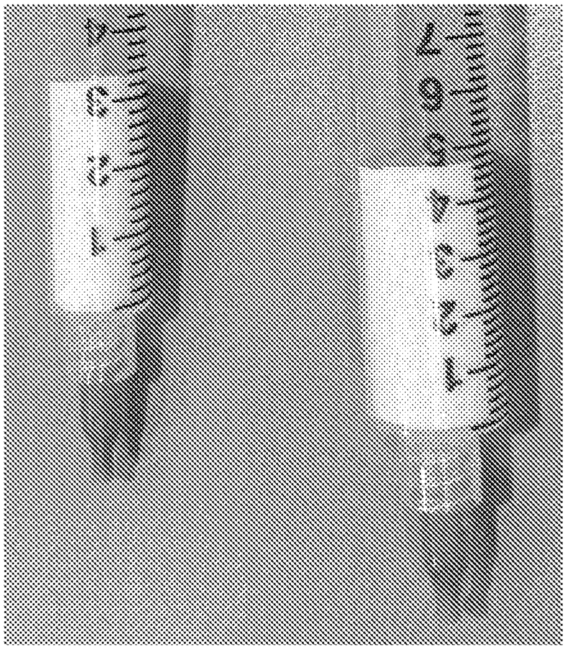
FIG. 6B shows a further aspect of the present disclosure, wherein a porous material membrane is placed within a cylinder that can operably connect to a vacuum and sealed for vitrification of a sample placed on the membrane, with the membrane providing the capillary substrate for vitrification.

As described herein, capillaries may be provided by patterning or contouring the walls of a desiccation chamber to effectively provide an underlying capillary bed (see, e.g., FIGS. 1B and 6A) or by providing a porous material of a contiguous capillary network, such as with a membrane (see, e.g., FIG. 3). In some aspects, the capillary network provided by a porous material and/or a patterned and/or contoured surface features pores of about 20 μm or less, such that the pores provide underlying capillaries to assist in vitrification. In some aspects, the pores or peak to peak distance in an undulating bed may be of an average opening of from about 20 μm to about 0.1 μm, including about 19, 18, 17, 16, 15, 14, 13, 12, 11, 10, 9, 8, 7, 6, 5, 4, 3, 2, 1.0, 0.9, 0.8, 0.7, 0.6, 0.5, 0.4, 0.3, and 0.2 μm. A capillary channel may have a length optionally defined by the thickness of a substrate that forms the channels or by one or a plurality of individual channels themselves. A capillary channel length is optionally about one millimeter or less, but is not to be interpreted as limited to such dimensions. Optionally, a capillary channel length is of about 0.1 microns to about 1000 microns, or any value or range therebetween. Optionally, a capillary channel length is of about 5 to about 100 microns, optionally of about 1 to about 200 microns, and/or optionally of about 1 to about 100 microns. A capillary channel length is optionally about 5, 10, 15, 20, 25, 30, 35, 40, 45, 50, 55, 60, 65, 70, 75, 80, 85, 90, 95, or 100 microns. In some aspects, the length of the capillary channels varies throughout a plurality of capillary channels, optionally in a non-uniform variation.

The cross-sectional area of the capillary channel(s) may be of about 2000 $\mu m^2$ or less. Optionally a cross-sectional area is of about 0.01 $\mu m^2$ to about 2000 $\mu m^2$, optionally of about 100 $\mu m^2$ to about 2000 $\mu m^2$, or any value or range therebetween. Optionally, a cross-sectional area of the capillary channel(s) is of about 100, 200, 300, 400, 500, 600, 700, 800, 900, 1000, 1100, 1200, 1300, 1400, 1500, 1600, 1700, 1800, 1900, or 2000 $\mu m^2$ or less.

Capillary assisted evaporation rate may be affected by both atmospheric demand (humidity, temperature and velocity of air/gas at the evaporating surface), and (i) the characteristics of the capillary channels that generate the driving capillary force, (ii) the liquid meniscus depth, and (iii) the viscous resistance to flow through the capillary. Consequently, complex and highly dynamic interactions between capillary properties, transport processes, and boundary conditions result in wide range of evaporation behaviors. For fast drying the key parameters may include: (1) the conditions that support formation and sustain a liquid network at the evaporating surface and (2) the characteristics that promote formation of capillary pressure that induce sufficient flow to supply water at the evaporating surface.

In some aspects, the porous material may be ridged and/or contoured or placed upon a ridged and/or contoured underlying support substrate, such that the porous material adopts a similar shape when placed or pressed thereon. The contours and/or ridges of a patterned material may increase surface area to provide for increased exposure for evaporation.

In further aspects, increased surface area of the porous material can be achieved by arranging or shaping a membrane. As set forth herein, a desiccation chamber with contoured walls may provide an increased surface area for the porous material. However, shaping an otherwise flat porous material can further provide improved surface area for efficient capillary assisted evaporation (see, e.g., FIGS. 6A and B).

In some aspects, the membrane is hydrophilic. It will be appreciated that mRNA may be soluble in water or water-based solutions. In some instances, the mRNA is in solution inside of a lipid or an LNP or similarly based vehicle as described herein. It can therefore be beneficial to have a capillary network that does not repel aqueous solutions. It can also be beneficial to have a hydrophilic capillary system to isolate expelled water from an mRNA composition as it desiccates. It will be further appreciated that rapid and/or efficient absorption of aqueous solutions from the mRNA or mRNA compositions and/or vitrification medium will prevent or reduce the chance for resolubilization and/or reabsorption improve the overall vitrification process.

Figure 9:
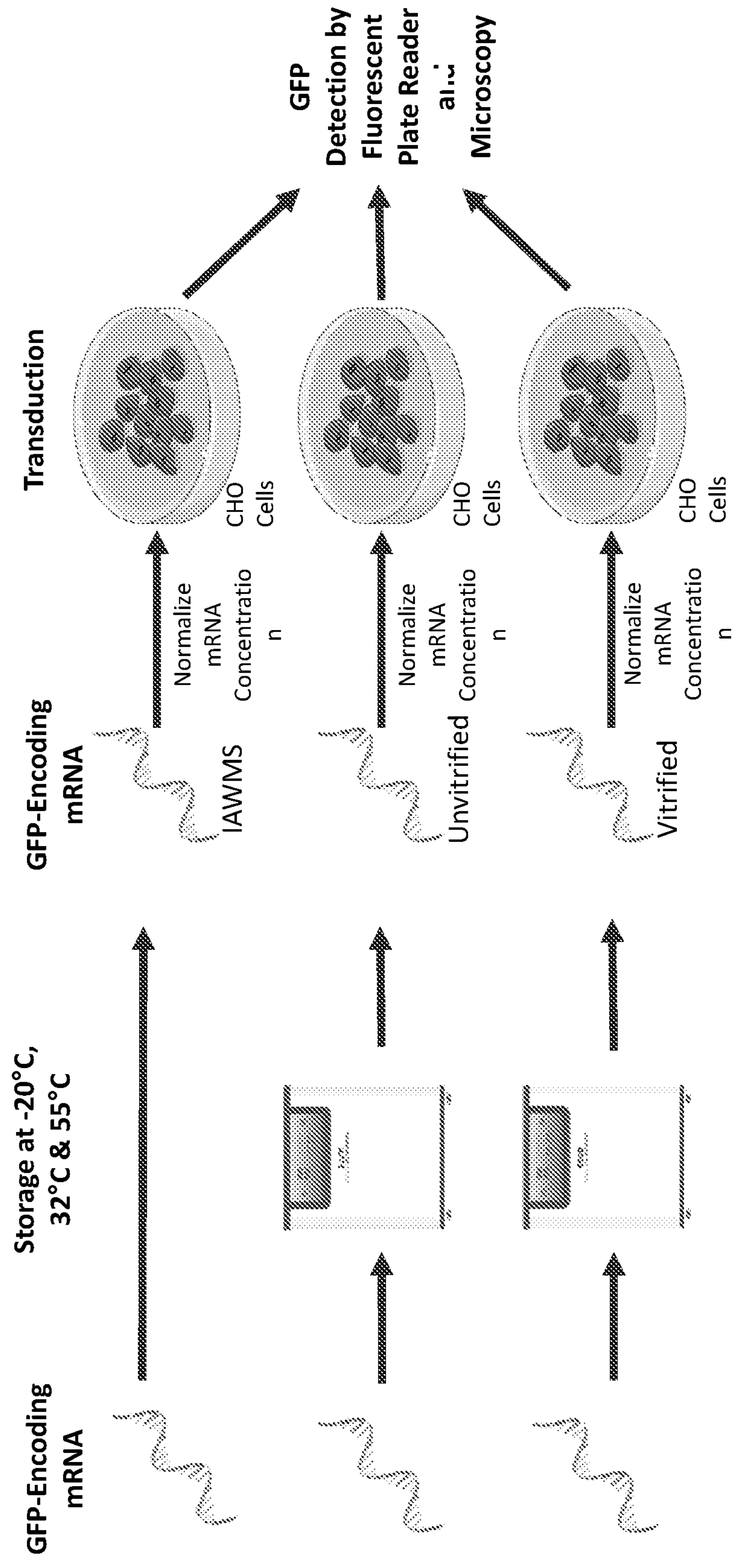
FIG. 9 shows an overview for the assessment of the vitrification on mRNA samples for an exemplary two-week course of study. mRNA is vitrified or unvitrified and stored as indicated and assessed after 0, 1, 3, 7 and 14 days as described herein and then normalized and transduced into cells. At each time point, fresh mRNA constituted according to the manufacturer's instructions is also assessed as a control point of comparison (IAWMS=in accordance with manufacturer's specifications).

In some aspects, the capillary network is of a hydrophilic material. In other aspects, the capillary network may be of a hydrophobic material and further treated to be hydrophilic or more hydrophilic in nature, such as through plasma treating. As depicted in FIG. 9, an originally hydrophobic membrane was treated with cold plasma to render it more hydrophilic. Upon drug formulation suspension on the membrane, the liquid formed a nearly spherical droplet (top left) whereas the hydrophilic membrane allowed the liquid to flow into the underlying capillary channels. During the vitrification process, the liquid droplet on the hydrophobic membrane first boiled and then froze, whereas the liquid on the hydrophilic membrane vitrified quickly forming a glassy monolith. Upon the release of vacuum, the frozen droplet turned into liquid again, however the size was reduced to partial moisture loss. The efficacy of capillary evaporation on vitrification is evident in the even vitrification seen with the hydrophilic membrane.

Vitrification Methods

In some aspects, the lipid particle, lipid particle housing one or more cargo molecules, mRNA, mRNA composition, or mRNA vaccine composition is coated or immersed in a vitrification medium and placed on a support substrate providing capillary action to retain such during the steps of vitrification as set forth herein. In certain aspects, the capillary network absorbs some of the vitrification mixture while allowing a thin layer of fluid to remain above the membrane. In further aspects, the lipid particle, lipid particle housing one or more cargo molecules, mRNA, mRNA composition, or mRNA vaccine composition become vitrified as the pressure is lowered around the vitrification mixture. Application of heat will prevent crystallization of the mRNA or compositions thereof or vitrification medium while application of a heat gradient across the capillary network will prevent boiling, all collectively allowing for even and complete vitrification of the mRNA and/or compositions thereof.

In some aspects, the present disclosure concerns methods for vitrifying at least one lipid particle, lipid particle housing one or more cargo molecules, mRNA, mRNA composition, or mRNA vaccine composition. The methods include preparing an lipid particle, lipid particle housing one or more cargo molecules, mRNA, mRNA composition, or mRNA vaccine composition. For example, a vitrification mixture of a lipid particle, lipid particle housing one or more cargo molecules, mRNA, mRNA composition, or mRNA vaccine composition and a vitrification medium is placed on or in contact with a solid support substrate. In some aspects, the underlying solid support is contoured and/or ridged to provide an underlying capillary network. In some aspects, the underlying support is part of a desiccation chamber, such as a wall thereof. In other aspects, a porous membrane can be placed between the vitrification mixture and a solid support. In some aspects, a contiguous capillary network supports the vitrification mixture and draws in fluid therefrom. The capillary network and/or porous material is to be of a sufficient thickness or quantity so as to avoid the presence and/or pooling of liquid above the surface of the capillary network.

The methods of vitrification of the present disclosure further include placing the vitrification mixture containing the lipid particle, lipid particle housing one or more cargo molecules, mRNA, mRNA composition, or mRNA vaccine composition in a desiccation chamber, the desiccation chamber being operably connected to a vacuum or other means for reducing the atmospheric pressure therein. In certain aspects, the vitrification mixture is held in place on a porous or contoured material within the desiccation chamber. In some aspects, the vitrification mixture is placed on part of the desiccation chamber, wherein the part is patterned and/or contoured so as to providing an underlying capillary network. In some aspects, a solid support substrate, a porous material, such as a membrane, and the vitrification mixture are placed in the desiccation chamber.

In some instances the lipid particle, lipid particle housing one or more cargo molecules, mRNA, mRNA composition, or mRNA vaccine composition may be coated and/or mixed with a vitrification medium in the desiccation chamber. In other aspects, the lipid particle, lipid particle housing one or more cargo molecules, mRNA, mRNA composition, or mRNA vaccine composition may be prepared with a vitrification medium prior to placement within the desiccation chamber.

Once assembled, the methods of the present disclosure may include reducing atmospheric pressure around the vitrification mixture, providing capillary-assisted evaporation to the vitrification mixture and/or applying heat energy to the vitrification mixture without inducing boiling therein or freezing of the vitrification mixture or any component housed therein. As described herein application of all three can provide for rapid and even vitrification and desiccation of the vitrification mixture, while avoiding experiencing a cryogenic temperature and avoiding boiling, thereby significantly reducing any damage to the lipid particle, lipid particle housing one or more cargo molecules, mRNA, mRNA composition, or mRNA vaccine composition thereof during the process and significantly improving activity of the lipid particle, lipid particle housing one or more cargo molecules, mRNA, mRNA composition, or mRNA vaccine composition following reconstitution.

In some aspects, the methods of the present disclosure concern applying a low atmospheric pressure to the vitrification mixture on the capillary network. In some aspects, a low pressure is applied while further providing heat to avoid the lipid particle experiencing a freezing condition, lipid particle housing one or more cargo molecules, mRNA, mRNA composition, or mRNA vaccine composition. The present disclosure concerns a vitrification process that combines low atmospheric pressure and heat energy to achieve even and rapid vitrification of the vitrification mixture. In some aspects, the present disclosure concerns application of heat energy to a vitrification mixture vitrification occurs under reduced atmospheric pressure. In some aspects, heat energy is applied to a vitrification mixture to prevent the crystallization of the vitrification mixture.

Once the vitrification mixture is placed within the desiccation chamber, the atmospheric pressure therein is lowered. In some aspects, the atmospheric pressure is lowered to a point above that of the triple point of the vitrification mixture or lipid particle, lipid particle housing one or more cargo molecules, mRNA, mRNA composition, or mRNA vaccine composition therein. In other aspects, the atmospheric pressure is lowered to a point above that of the triple point of water. In further aspects, the pressure is lowered within the desiccation chamber to about 0.04 atm.

In some aspects, the heat energy is applied to a vitrification mixture as it undergoes vitrification on a capillary network. In some aspects, an underlying capillary network can allow for even and complete vitrification of a vitrification mixture receiving heat energy while protecting the vitrification mixture from boiling. The capillary network can be a contiguous network of capillaries. In some instances, the capillary network can be provided by an underlying porous material, such as a membrane, or an underlying contoured or ridged surface wherein the troughs and peaks thereof provide a bed sufficient to subject a liquid vitrification mixture to capillary action during vitrification.

Figure 2A:
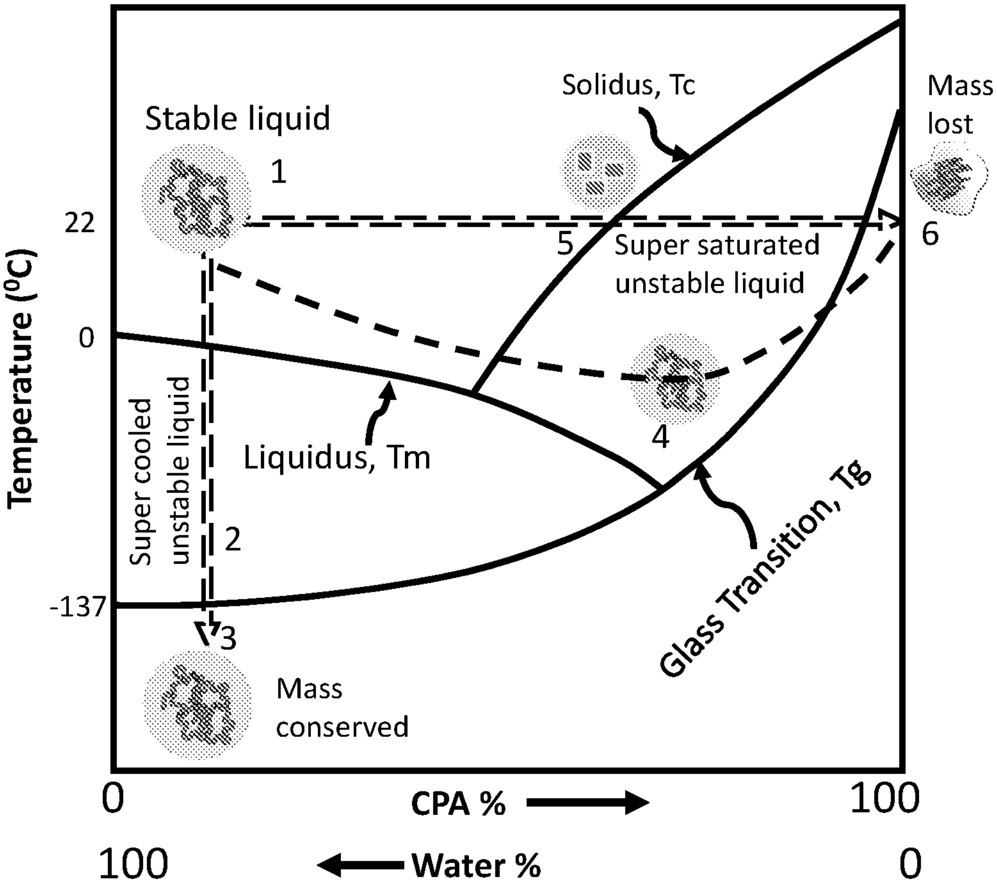
FIG. 2A shows a generalized schematic of vitrification according to some aspects as provided herein. Cryogenic vitrification is historically achieved by fast cooling a liquid (pathway 1-2-3) (containing biological or other materials) to below the glass transition temperature bypassing the freezing zone. The total mass of the material is conserved through the process. Similarly, vitrification of materials can be achieved by fast desiccation bypassing the crystallization process (pathway 1-5-6). In this case, significant mass loss (primarily water) occurs. Cryogenic vitrification of a large amount material can be challenging due to heat transfer limitations and hence generally carried out in vials that provide significant surface/volume ratio. Similarly, fast desiccation is facilitated by large surface/volume ratio and specifically at reduced pressure. Reduction of pressure also reduces the boiling point of the liquid, which risks undesirable boiling of the liquid while vitrifying sensitive biomolecules or materials. The pathway of 1-4-6 shows the schematic of some vitrification aspects the present disclosure, where the application of heat and low atmospheric pressure allow for fast vitrification avoiding freezing temperature exposure.

FIG. 2A is an overview of an exemplary aspect of the vitrification process of the present disclosure. Traditional vitrification is demonstrated in the pathway 1-2-3 where fast cooling a liquid (containing biological or other materials) to below the glass transition bypasses the freezing zone. The total mass of the material is conserved through the process. Cryogenic vitrification of a large amount material can be challenging due to heat transfer limitations and hence is generally carried out in vials that provide significant surface/volume ratio. Vitrification of materials can also be achieved by desiccation (bypassing the crystallization process), seen in pathway 1-5-6. In this aspect, significant mass loss (primarily water) occurs. Traditional dehydration approaches for biological materials have centered on establishing a sessile droplet on a substrate and evaporatively desiccating in a low humidity enclosure. The process is marked by a slow pace and uneven desiccation. A glassy skin forms at the interface between the liquid and vapor as the biological material therein desiccates. The formation of the glassy skin slows and ultimately prevents further desiccation of the vitrification mixture, thereby limiting the vitrification mixture to only a certain level of dryness with significant spatial non-uniformity of water content across the sample. As a result, some regions are not vitrified but will now degrade due to retained high molecular mobility. The desiccation rate can be facilitated by a large surface to volume ratio and specifically at reduced pressure.

Figure 2B:
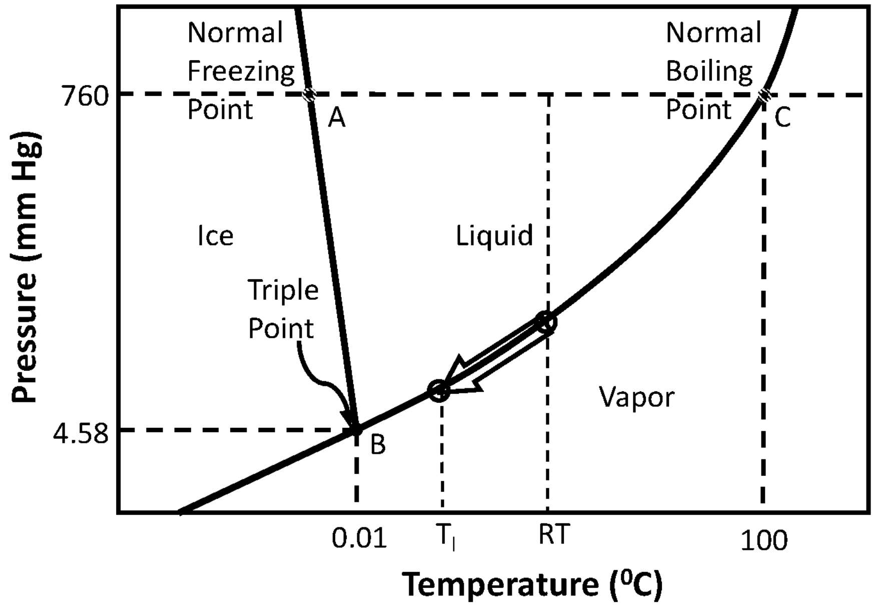
FIG. 2B shows a schematic of the triple point for water with a targeted sample temperature Ti avoiding the triple point and hence freezing during vitrification.

In some aspects, the present disclosure concerns pathway 1-4-6 of FIG. 2A, where maintaining a desired temperature of the vitrification mixture and low pressure offer a hybrid of near cryogenic temperature and desiccation. However, with lower pressure, the boiling point is reduced. As shown in FIG. 2B, keeping the low pressure above the triple point of water can provide a temperature window between freezing and boiling for vitrification of the vitrification mixture. In some aspects of the present disclosure, the applied temperature maintains the temperature above the cryogenic point of the vitrification mixture at the low applied pressure. As further depicted in FIG. 2 and FIG. 4, the reduction in temperature from the applied low ambient pressure allows the temperature of the vitrification mixture to fall below the glass transition temperature without boiling, providing for even vitrification throughout the vitrification mixture.

FIG. 4A shows how fast desiccation of larger volumes of liquid can be conveniently achieved under vacuum by deploying a porous material of a network of capillaries to facilitate capillary evaporation, such as through the introduction of a membrane of contiguous capillary channels. When the liquid accumulates on the surface of the capillary membrane, however, boiling still can occur in the accumulated liquid, which as described herein can be undesirable. The presence of a temperature gradient between the surface and the bulk liquid allows for capillary evaporation as illustrated in the FIGS. 4E and 4F, where the fast evaporation can be achieved.

Accordingly, in some aspects of the present disclosure, the volume of fluid present in the vitrification mixture can be established such the fluid can fill the capillary network without overflowing or pooling on the surface.

Figure 5:
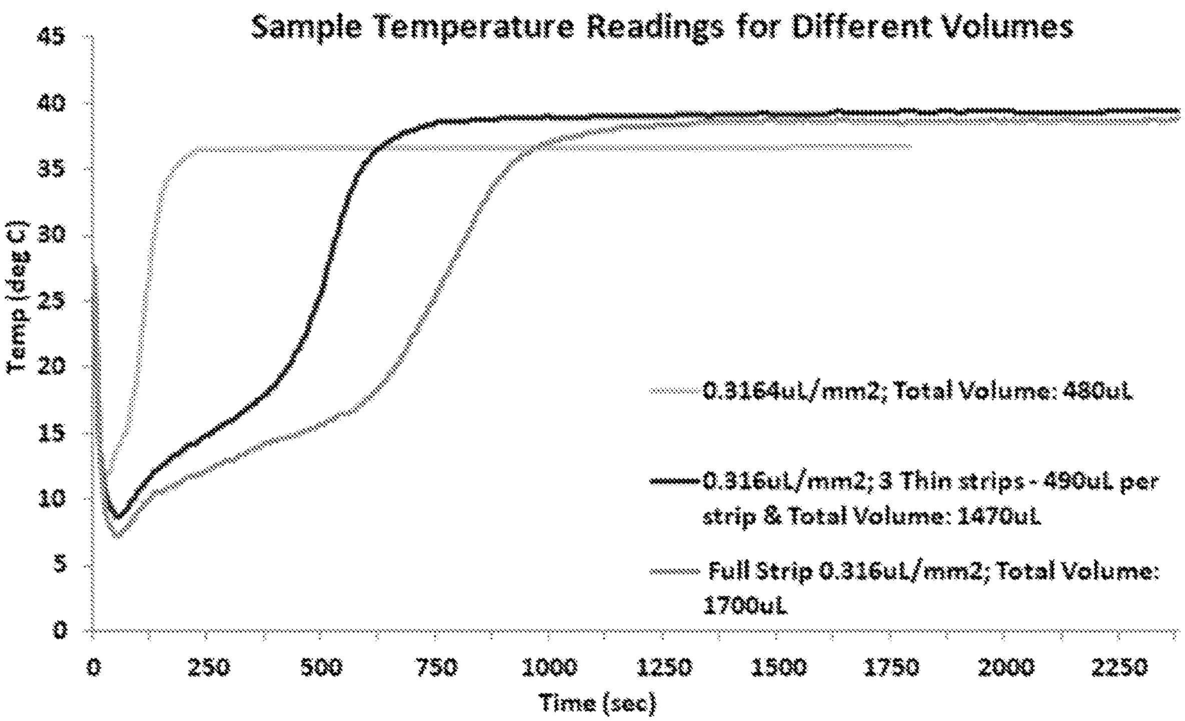
FIG. 5 shows vitrification results for glass membranes of different dimensions loaded with a liquid containing 4% BSA, 15% Trehalose Dihydrate, 0.75% Glycerol, 2% Tween-20, and water. The liquid loading per $mm^2$ of the membrane was kept at 0.316 ml for all cases. For Case 1, the membranes were cut into 0.25 inch diameter circles and each was loaded with 10 μl liquid. A total of 48 samples containing 480 μl was loaded on a heated (37° C.) wire mesh inside a vacuum chamber. For Case 2, three long membrane strips (240 mmx 6.23 mm) each containing 470 μl liquid were loaded on the heated wire mesh. For case 3, a single strip (240 mm×22 mm) containing 1700 μl liquid was utilized. The chamber was evacuated to 29.5 mmHg. The temperature-time plots indicate the stages of the vitrification process. At the onset of the evacuation process, the pressure drops quickly while the membranes' scaffold contains mostly liquid and as expected the temperature drops with the pressure drops. The supplied heat flux from the wire mesh/bed prevents further drop of the scaffold temperature into freezing regime. It is to noted that the freezing point can extend into subzero temperatures depending on the formulation of the vitrification excipient/liquid. Besides preventing freezing, the supplied heat flux from the bed also facilitates capillary evaporation while preventing boiling of the liquid under reduced pressure as illustrated above (FIG. 4F). As the moisture evaporates from the scaffold, the temperature rises until it reaches the bed temperature. The heat flux is controlled so that the scaffold temperature does not go above a set temperature, usually the bed temperature. As seen from FIG. 5, the time taken for the membrane scaffold temperature to reach the bed temperature varies with the scaffold configuration as well as the amount of liquid loaded onto it. The time taken to reach the bed temperature is a measure of the primary vitrification time meaning majority of the liquid is evaporated in this period. However, desiccation process still may prolong beyond this period to remove some residual moisture, which can be termed as secondary desiccation, which is not dependent the capillary phenomena. The process parameters and the scaffold geometry are chosen to optimize the volume of the liquid that can undergo primary desiccation process in a given time. In general, faster desiccation rate is desirable to bypass the crystal precipitation phase boundary indicated in FIG. 2A and to ensure glass formation. However, there is threshold rate above which vitrification is ensured which depends on the chemistry of the liquid, the membrane characteristics such as hydrophilicity, porosity and dimensions.

FIG. 5 depicts results seen from applying 37° C. heat from a wire mesh as the underlying solid support and glass membranes thereon as the porous material. FIG. 5 shows a comparison between the membrane and volume size and the rate at which the sample temperature recovers following lowered pressure when liquid loading is maintained constant. As set forth in FIG. 5, in all cases, application of the vacuum leads to a rapid drop of temperature of the vitrification mixture, yet the smaller membranes produced faster complete vitrification as observed by return to the starting temperature. With further reference to FIG. 5, it is seen that the temperature of the sample plateaus once vitrification is complete.

In some aspects, the methods of the present disclosure include providing capillary assisted evaporation of a vitrification mixture. In some aspects, the underlying capillary network provided by a contoured and/or ridged support or by a porous membrane will provide the necessary features required to enhance evaporation.

In some aspects, the methods of the present disclosure may be performed for a desiccation time. A desiccation time is a time sufficient to promote suitable drying to vitrify the vitrification medium. A desiccation time is optionally from about 1 second to about 1 hour, including but optionally not exceeding about 10 s, 30 s, 1 min, 5 min, 10 min, 20 min, 25 min, 30 min, 35 min, 40 min, 45 min, 50 min and 55 min.

Optionally, a desiccation time is of from about 1 second to about 30 min, optionally of from about 5 seconds to about 10 min.

Vitrified Compositions

In some aspects, the present disclosure concerns vitrified lipid particle, lipid particle housing one or more cargo molecules, mRNA, mRNA composition, or mRNA vaccine composition. The vitrified mRNA vaccine compositions may include at least one single stranded mRNA molecule encapsulated in a lipid nanoparticle (LNP) or a lipid-like-nanoparticle. In some aspects, the vitrified mRNA vaccine composition can further include vitrified vitrification medium, such as around or near the mRNA in the LNP or LLN and/or around the LNP or LLN to provide stability thereto. The LNP and/or LLN may include an ionizable lipid, optionally with a cholesterol, a PEG and/or a helper lipid, such as DOTAP, DOPE, DOPC and the like. In some aspects, the vitrified mRNA composition may be affixed through the vitrified or desiccated vitrification medium to a capillary network, such as a membrane.

Storage

In certain aspects, the present disclosure concerns handling and storage of the vitrified lipid particle, lipid particle housing one or more cargo molecules, mRNA, mRNA composition, or mRNA vaccine composition. As with all materials utilized, care can be taken to avoid exposing the vitrified compositions to potential sources of degradative enzymes including RNAse both during the vitrification process and in any handling, storage or reconstitution steps taken thereafter.

Following the vitrification steps, the lipid particle, lipid particle housing one or more cargo molecules, mRNA, mRNA composition, or mRNA vaccine composition will be effectively preserved in a dehydrated state in the vitrification medium on the capillary membrane. The vitrified molecules can remain thereon and moved to a sealed environment. In aspects where the vitrification mixture is within a desiccation chamber, the capillary network or the desiccation chamber itself can be moved to a sealed or closed environment to protect the lipid particle, lipid particle housing one or more cargo molecules, mRNA, mRNA composition, or mRNA vaccine composition from humidity and exposure to degradative enzymes.

In some aspects, the vitrified lipid particle, lipid particle housing one or more cargo molecules, mRNA, mRNA composition, or mRNA vaccine composition can be then stored in any desired temperature. As the lipid particle, lipid particle housing one or more cargo molecules, mRNA, mRNA composition, or mRNA vaccine composition is in a dehydrated state, exposure to sub-cryogenic temperatures at this point will not result in the same crystallization as could be expected pre-vitrification as the ability of the molecules therein to rearrange into a crystal structure is negated due to the dehydrated, vitrified state of the molecules therein. Accordingly, the vitrified lipid particle, lipid particle housing one or more cargo molecules, mRNA, mRNA composition, or mRNA vaccine composition can be stored at about −80° C. to at about −20° C. to at about −5° C. to at about 0° C.

The storage of the vitrified lipid particle, lipid particle housing one or more cargo molecules, mRNA, mRNA composition, or mRNA vaccine composition does not need to be at zero or subzero temperatures to retain structural integrity and activity. As demonstrated herein, the lipid particle, lipid particle housing one or more cargo molecules, mRNA, mRNA composition, or mRNA vaccine composition can be stored for prolonged periods at room temperatures (e.g. about 20 to about 34° C.) for periods extending into at least months without significant loss in structural integrity or functional activity (e.g. translation of the mRNA). The vitrified lipid particle, lipid particle housing one or more cargo molecules, mRNA, mRNA composition, or mRNA vaccine composition may also be stored at higher temperatures, including up to about 50, 55, or 60° C. for extended periods of time, including weeks and months.

In other aspects, the vitrified lipid particle, lipid particle housing one or more cargo molecules, mRNA, mRNA composition, or mRNA vaccine composition need not be stored at a constant or near constant temperature in order to retain functional activity, including withstanding season fluctuations from subfreezing to 40° C. or higher, including up to 60° C. or higher.

Those skilled in the art will appreciate that storage can be prolonged with improved or deliberate prevention of exposure to significant environments with high humidity, particularly at high temperatures. As the lipid particle, lipid particle housing one or more cargo molecules, mRNA, mRNA composition, or mRNA vaccine composition are in a vitrified state, preventing exposure to moisture can prolong and preserve the ability to be reconstituted without any expectation of loss of functional activity. The more that vitrified lipid particle, lipid particle housing one or more cargo molecules, mRNA, mRNA composition, or mRNA vaccine composition is allowed to absorb water from an ambient atmosphere, the quicker that a compromise in activity or retained structure can be expected.

In some aspects, storage of the lipid particle, lipid particle housing one or more cargo molecules, mRNA, mRNA composition, or mRNA vaccine composition can include sealing and/or the inclusion of desiccants to aid in prevent any absorption of water from a surrounding atmosphere. In some aspects, the lipid particle, lipid particle housing one or more cargo molecules, mRNA, mRNA composition, or mRNA vaccine composition may remain viable while in storage above cryogenic temperature for 2-20 days. In other aspects, the lipid particle, lipid particle housing one or more cargo molecules, mRNA, mRNA composition, or mRNA vaccine composition may remain viable while in storage above cryogenic temperature for 10 weeks. In other aspects, the lipid particle, lipid particle housing one or more cargo molecules, mRNA, mRNA composition, or mRNA vaccine composition may remain viable in storage above cryogenic temperature for up to one year. In other aspects, the lipid particle, lipid particle housing one or more cargo molecules, mRNA, mRNA composition, or mRNA vaccine composition may remain viable while in storage above cryogenic temperature for up to 10 years.

Reconstitution

In some aspects, the present disclosure may include reconstituting and/or purifying the lipid particle, lipid particle housing one or more cargo molecules, mRNA, mRNA composition, or mRNA vaccine composition molecules and compositions as disclosed herein. In some aspects, the lipid particle, lipid particle housing one or more cargo molecules, mRNA, mRNA composition, or mRNA vaccine composition can be purified by reconstitution with an aqueous solution such as water or a salt and/or buffered water solution, or a solution that includes an encapsulating compositions such as lipids to form lipid nanoparticles, cholesterol, etc. Purification of the reconstituted material, if desired, may include chromatographic methods, such as use of a poly(T) or poly(U) coupled resin to bind the mRNA, followed by denaturing elution with high salt and/or high pH.

In some aspects, the present disclosure concerns eluting the lipid particle, lipid particle housing one or more cargo molecules, mRNA, mRNA composition, or mRNA vaccine composition from the capillary network or membrane. Elution can be achieved by rehydration with sterile or purified water or a sterile/purified saline or buffered solution or an aqueous media, such that the vitrified materials are allowed to reabsorb water and return to a native state. In some aspects, reconstitution of the lipid particle, lipid particle housing one or more cargo molecules, mRNA, mRNA composition, or mRNA vaccine composition will result in their presence in the reconstituting medium and the underlying capillary system can be removed or isolated therefrom.

The present disclosure concerns in some aspects of adding the reconstituted lipid particle, lipid particle housing one or more cargo molecules, mRNA, mRNA composition, or mRNA vaccine composition to a further composition, such as a vaccine composition or adding a vehicle thereto for assisting with administration to a subject. While the present disclosure concerns in part the vitrification of lipid particle, lipid particle housing one or more cargo molecules, mRNA, mRNA composition, or mRNA vaccine composition, it is a further aspect to vitrify lipid particle, lipid particle housing one or more cargo molecules, mRNA, mRNA composition, or mRNA vaccine composition and, following reconstitution, add further components needed to perfect the composition, such as for administration to a subject. Such later steps may include encapsulating the mRNA in compositions as set forth herein and/or adding additional vehicles, such as an adjuvant. For example, mRNA can be reconstituted and then mixed with a lipid or components of an LNP to allowed for encapsulation of the reconstituted mRNA.

A reconstituted lipid particle, lipid particle housing one or more cargo molecules, mRNA, mRNA composition, or mRNA vaccine composition may be administered either systemically or locally to a subject to induce an immune response to an exogenous target. As used herein, a "subject" is an animal, optionally human, non-human primate, equine, bovine, murine, ovine, porcine, rabbit, or other mammal. Optionally, a subject is a human. The vitrified mRNA may be reconstituted prior to administration, optionally immediately prior to administration, optionally within the syringe or other administration device at the point of administration or substantially near thereto. Administration may be oral, injection, nasal, vaginal, buccal, or other desired route of administration. Optionally, a reconstituted mRNA may be administered by injection, optionally intramuscular injection, intradermal injection, subcutaneous injection, intraperitoneal injection or intravenous injection.

Various aspects of the present disclosure are illustrated by the following non-limiting examples. The examples are for illustrative purposes and are not a limitation on any practice of the present invention. It will be understood that variations and modifications can be made without departing from the spirit and scope of the invention.

EXAMPLES

For the purposes of examining mRNA quantity and activity, an mRNA encoding a green-fluorescent protein (GFP) with a 5' cap1 structure and a poly(a) tail at the 3' end was obtained (Dasher GFP from Aldevron, Madison WI). The GFP was chosen as it provides a 26.6 kDa expressed protein with bright fluorescence to easily track and analyze mRNA delivery and expression in a cell or tissue.

To determine what effects the vitrification process might have on both mRNA quantity and mRNA activity, the following variables and controls were established and assayed:

- Fresh mRNA
- No mRNA/vehicle only
- Vitrified mRNA stored at −20° C.
- Unvitrified mRNA stored at −20° C.
- Vitrified mRNA stored at 28° C.
- Unvitrified mRNA stored at 28° C.
- Vitrified mRNA stored at 55° C.
- Unvitrified mRNA stored at 55° C.

In all cases, mRNA was examined after 3, 7 and 14 days of storage at the identified conditions (where appropriate). RNA was quantified by 260/280 nm light spectrophotometry and activity was determined both visually and quantitatively by assaying relative fluorescence units. For GFP activity, CHO-K1 cells were transfected following collection/preparation and allowed 24 hours for expression. FIG. 9 sets for an overview of the storage and time conditions assessed, as well as the varying controls included for purposes of comparison and verification.

One day prior to the each day of assessment, cells were prepared and allowed to be established. 40,000 Chinese Hamster ovary (CHO) cells were plated per well in a 96-well flat, clear bottom tissue culture plated and stored at 2-4° C.

For the samples, 3 micrograms (μg) of mRNA was utilized to allow for adequate amounts of mRNA detection, while further assessing if lower end quantities could be adequately recovered.

For the vitrification process, the mRNA was mixed in a 1:1 ratio with a 2× vitrification medium (0.454 grams (g) trehalose, 0.023 g glycerol and 724 μL PBS) that had previously been sterilized through a 0.2 μm PES membrane filter. The vitrification mixture was allowed to vitrify in aseptic conditions on polyethersulphone (PES) disc membranes for 30 minutes in a covered petri dish with a wire mesh therein.

For storage, once vitrified, the tissue cassettes were inserted in foil pouches with a desiccant therein and vacuum sealed.

For the unvitrified samples, the stock mRNA was dispensed into microcentrifuge tubes, which were placed into foil pouches and vacuum sealed.

Each group, vitrified and unvitrified, were divided into groups for differing storage conditions (−20, 28 and 55° C.), with samples available to be obtained on days zero, 1, 3, 7 and 14.

For reconstitution of the vitrified samples, 50 μL of Fluorobrite DMEM was used applied to the mRNA to provide a maximum concentration of 60 ng/μL.

The mRNA concentration from the vitrified and unvitrified samples was then measured, along with a fresh mRNA sample that was prepared according to the manufacturer's instructions. The mRNA was then normalized with each to provide transduction of equal amounts of mRNA.

For transduction of the mRNA, protocols were followed according to the manufacturer (Lipofectamine Messenger MAX-ThermoFisher). Briefly, 1.25 μg of mRNA as incubated with 3.75 μL of media and 1.25 μL of Liopfectamine Messenger MAX was incubated with 3.75 μL of media and the two were then combined and allowed to incubate. 10 μL of the mRNA-lipofectamine mixture was then added/well of CHO cells. The cells were assessed one day after transduction by using a plate reader with excitation provided at 495 nm and detection at 525 nm. Cells were then imaged using a GFP (green) channel.

For each time point, cells were plated the day before the referenced time point and fluorescence assayed the day after transduction into the cells. For example, for day 0, cells were plated at day −1 and assessed for fluorescence at day 1. mRNA was reconstituted immediately following sealing in the foil pouch. For day 1, cells were plated on day 0 and fluorescence assayed on day 2. For day 3, cells were plated on day 2 and fluorescence assayed on day 4. For day 7, cells were plated on day 6 and fluorescence assayed on day 8. For day 14, cells were plated on day 13 and fluorescence assayed on day 15.

Day 0 Results:

Immediately after reconstitution, the vitrified mRNA concentration was measured using the standard 260/280 UV protocols. Table 1 sets for the mRNA concentrations obtained (expected is 60 ng/μL based on 3 μg being reconstituted in 50 μL).

TABLE 1

| mRNA Quantification | | |
|---|---|---|
| Name | ng/μL | 260/280 |
| Vitrified mRNA | 60.6 | 2.17 |
| Prepared mRNA | 62.1 | 2.24 |

Results obtained with fluorescence not shown.

Figure 10:
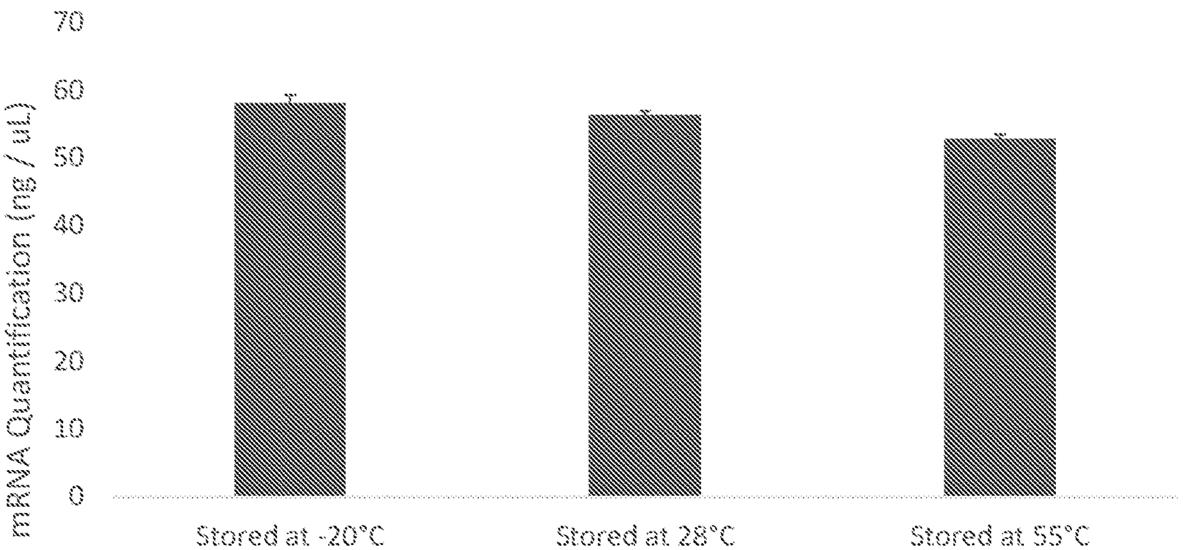
FIG. 10 shows the quantity of antigen-encoding mRNA retained following vitrification and storage is nearly identical to fresh demonstrating nearly 100% mass recovery. 60 ng/μL (3 μg in 50 μL) of mRNA was loaded per vitrification sample. Storage at a variety of environmental temperatures, ranging from −20° C. to 55° C., for up to 3 days resulted in a greater than 85% mRNA yield.
Figure 11:
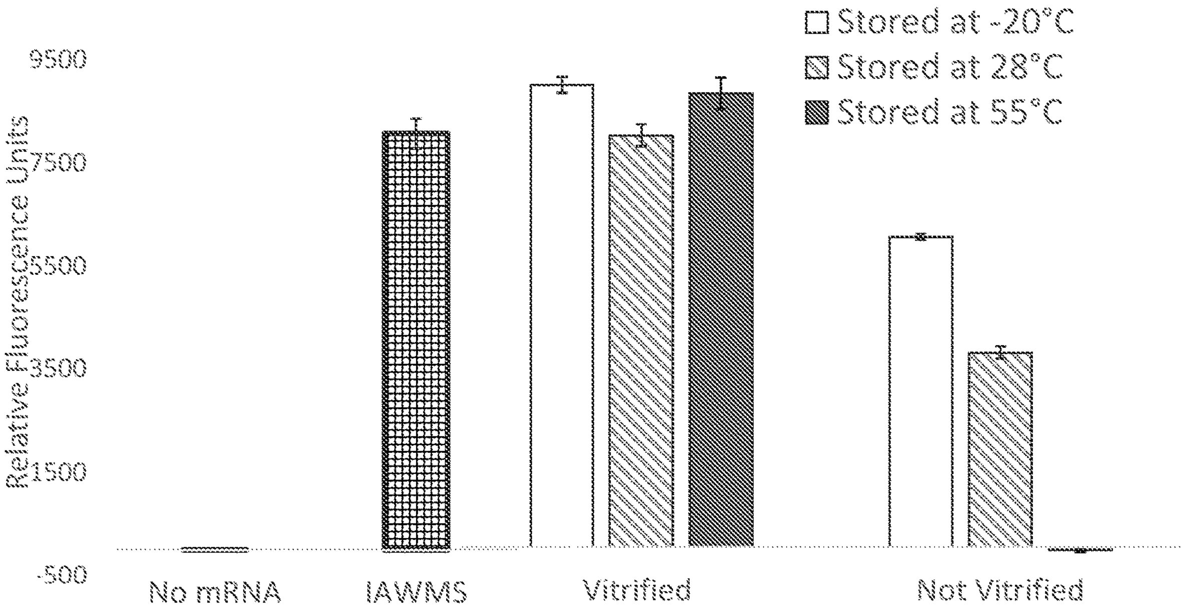
FIG. 11 shows that green fluorescent protein-encoding mRNA functionality is protected from degradation during storage for 3 days at a variety of environmental temperatures ranging from −20° C. to 55° C. The data presented compare relative fluorescence units for green fluorescent protein expression following transfection with the vitrified and unvitrified mRNA samples, stored at the indicated temperatures. The unvitrified samples show significant loss of fluorescence as the storage temperature increased, while the vitrified samples retained good activity even following storage at 55° C.
Figure 12:
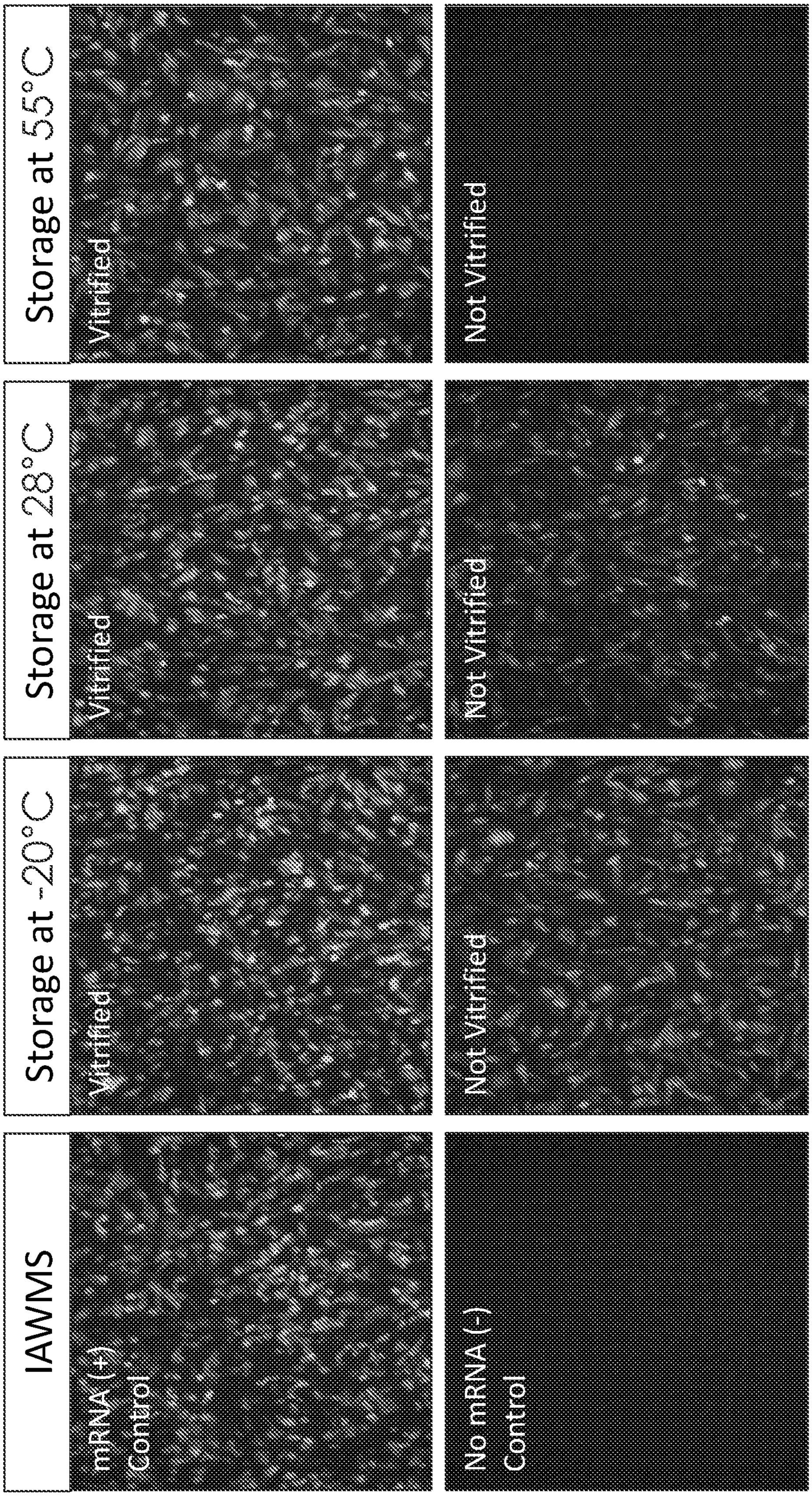
FIG. 12 shows representative fluorescent cell images for the indicated conditions taken at 3 days after storage commenced as set forth in FIG. 11.

Day 3 Results:

Immediately after reconstitution, the vitrified mRNA concentration was measured using the standard 260/280 UV protocols. FIG. 10 sets forth the mRNA concentrations obtained (expected is 60 ng/μL based on 3 μg being reconstituted in 50 μL). FIG. 11 sets forth the obtained fluorescence and FIG. 12 provides captured images of the observed fluorescence. Both show that after 3 days of storage, even at 55° C., the vitrified mRNA showed excellent concentration recovery and functional activity after transduction into CHO cells.

Day 7 Results.

Figure 13:
FIG. 13 shows day 7 fluorescence data for the vitrified and unvitrified samples, as well as fresh mRNA. Again the vitrification retained good activity despite the storage conditions, while the unvitrified samples showed significant loss of expression activity.
Figure 14:
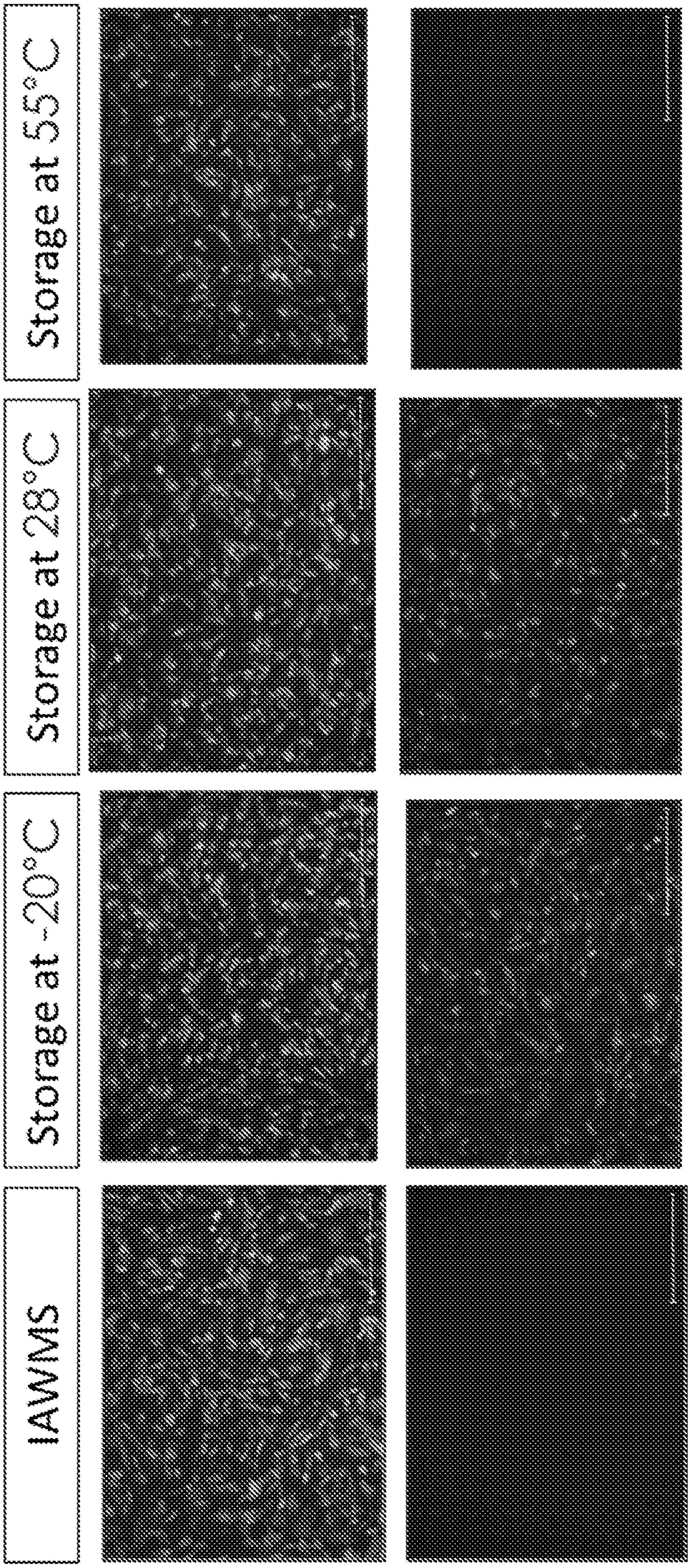
FIG. 14 shows representative images for the fluorescence presented in FIG. 13 with the same arrangement as provided in FIG. 12.

Immediately after reconstitution, the concentrations of mRNA were obtained (FIG. 13) and then transduced into CHO cells plated the day before. After 24 hours of incubation, the fluorescence was assayed (FIG. 14). Even with storage at 55° C., good mRNA was recovered and exhibited excellent in vitro activity, whereas unvitrified mRNA, even at −20° C. showed a poor yield and poor fluorescence.

Day 14 Results.

Figure 15:
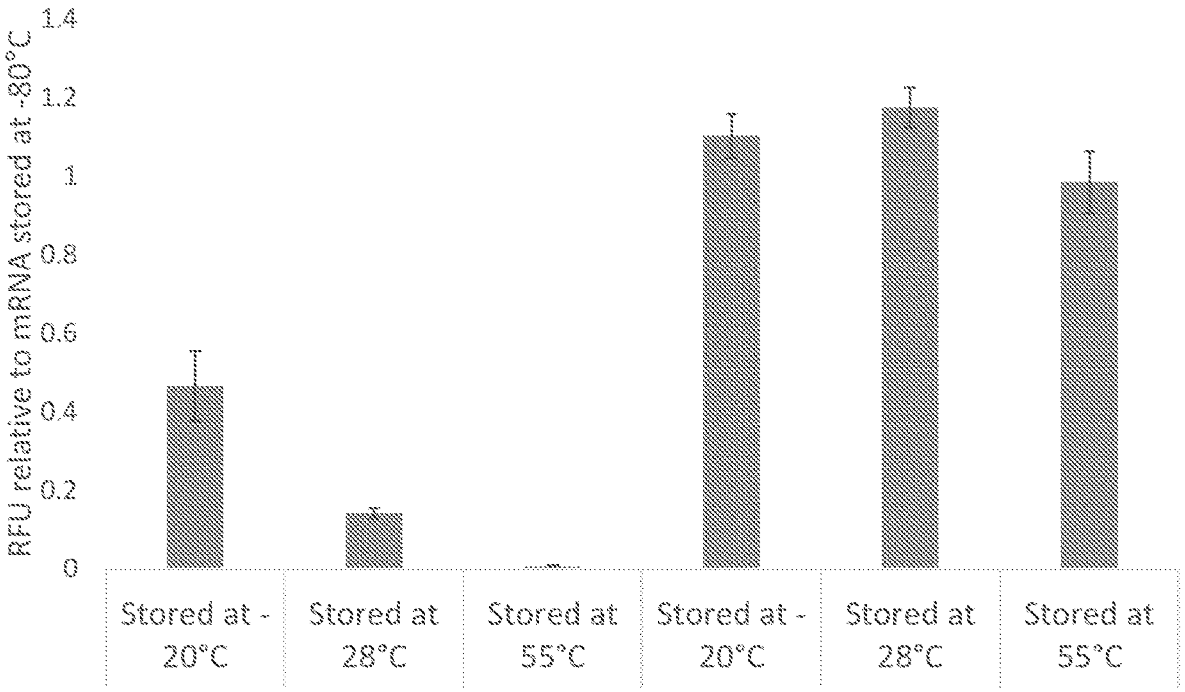
FIG. 15 shows day 14 fluorescence data for the vitrified and unvitrified samples. Again, the vitrification retained good activity despite the storage conditions, while the unvitrified samples showed significant loss of expression activity at all storage temperatures studied.
Figure 16:
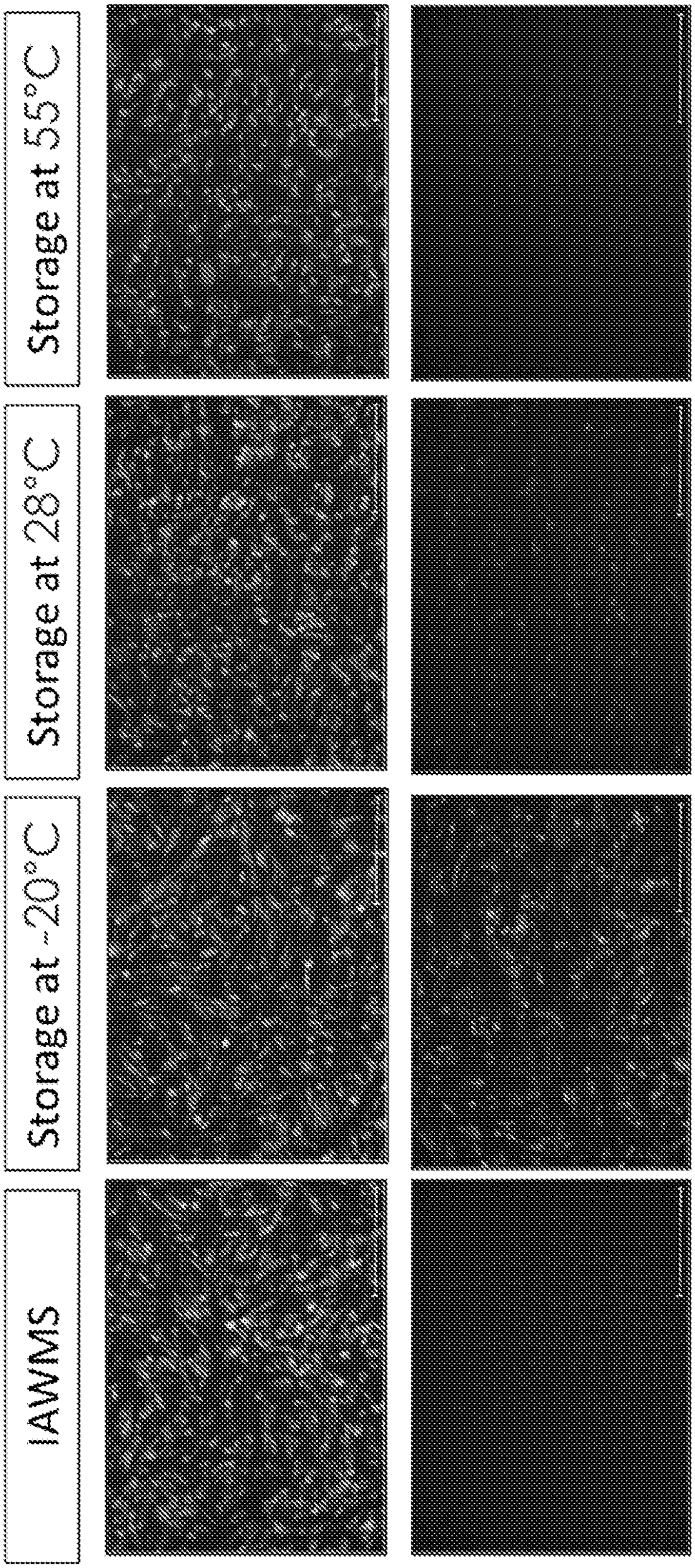
FIG. 16 shows representative images for the fluorescence presented in FIG. 15 with control samples on the left and vitrified samples on the top row with unvitrified samples stored as indicated on the bottom row.

On day 1, the concentration of mRNA obtained as illustrated in FIG. 15. Clearly recovery at all vitrified storage temperatures showed excellent recovery of the mRNA whereas without vitrification according to the processes as provided herein mRNA rapidly degraded. Similar results are observed with functional activity where vitrification allowed functional translational activity of the mRNA to be preserved, even following storage for 14 days at 55° C.

mRNA Vaccine Stability

Figure 7A:
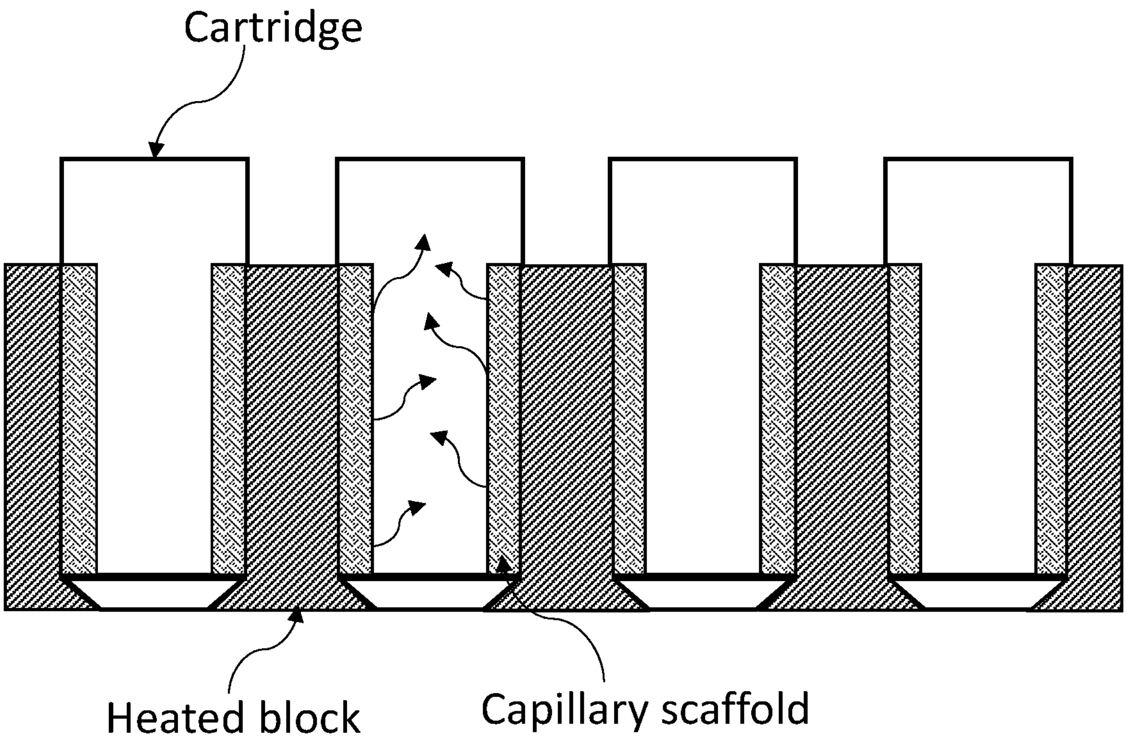
FIG. 7A illustrates one exemplary aspect of the present disclosure wherein the cylindrical desiccation devices are placed in a heated block to provide directional heat flux to promote capillary evaporation and preventing the scaffold temperature to fall into freezing regime. The heating method may be conductive or radiative in nature.
Figure 7B:
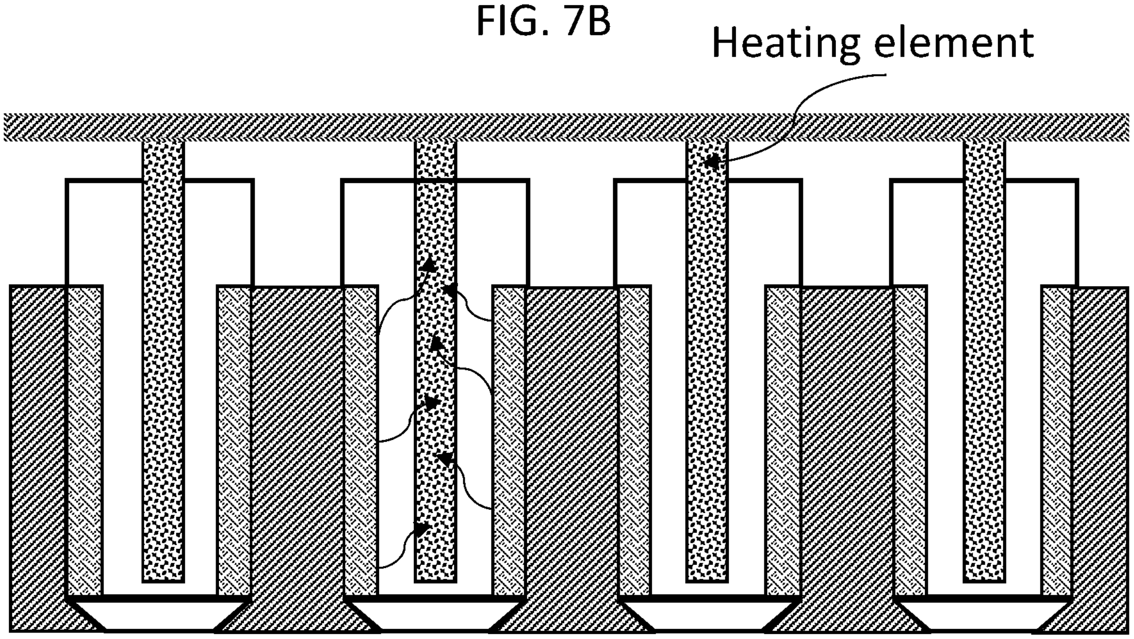
FIG. 7B illustrates one exemplary aspect of the present disclosure wherein additional heat source is provided from the inside of the cylinder. The heating method may be conductive or radiative in nature. The heat flux may be provided from one surface only or from both surfaces of the membrane.
Figure 8:
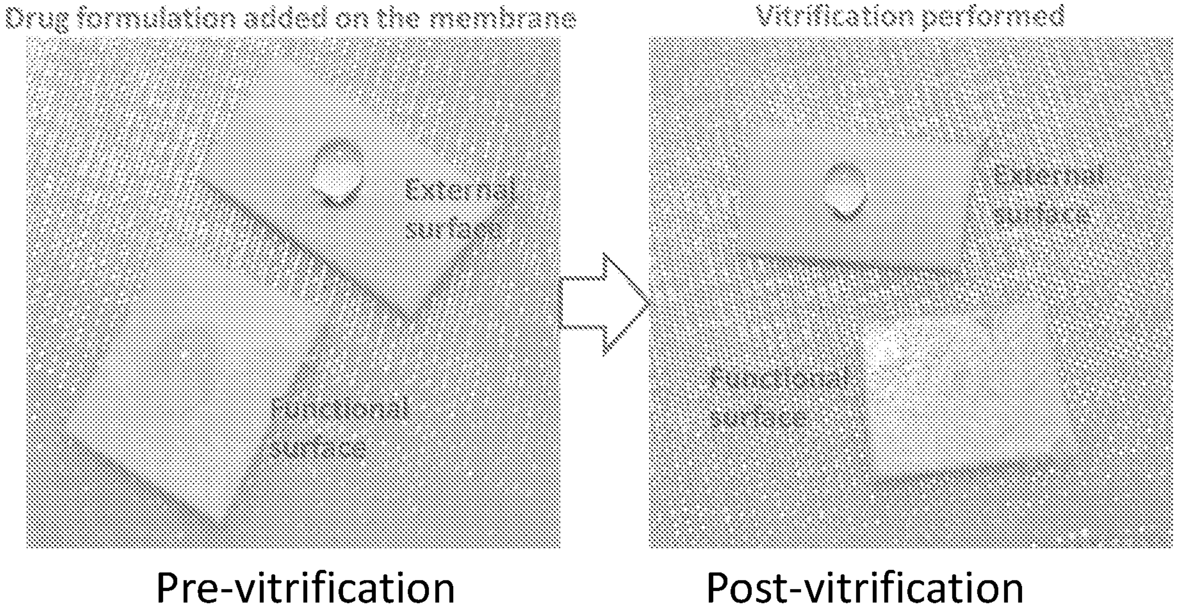
FIG. 8 illustrates improved vitrification produced using a membrane made of hydrophilic material. An originally hydrophobic membrane was treated with cold plasma to make it hydrophilic. Upon drug formulation suspension on the membrane, the liquid formed a nearly spherical droplet (top left) whereas the hydrophilic membrane allowed the liquid to flow into the capillary channels. During the vitrification process the liquid droplet on the hydrophobic membrane first boiled and then froze, whereas the liquid on the hydrophilic membrane vitrified quickly forming a glassy monolith. Upon the release of vacuum, the frozen droplet turned into liquid again, however the size was reduced due to partial moisture loss. The efficacy of capillary assisted evaporation on vitrification is apparent utilizing a hydrophilic membrane.

An mRNA encoding a desired antigen can be incubated with an ionizable lipid, optionally with a cholesterol, a PEG and a helper lipid to encapsulate the mRNA, or with Lipofectamine Messenger MAX (Invitrogen) and then incubated with a vitrification medium and placed on a PES membrane. The membrane was placed in a petri dish on a wire mesh to provide heat, or rolled into a syringe (as a cylindrical support) with a support scaffold to keep the membrane from directly resting on the walls of the syringe to allow for a heat gradient (see, FIGS. 7A and 7B). The syringe can then be placed in a heated block or have a heating element lowered therein.

The pressure of the system was then lowered to about 0.04 atm as heat at about 55° C. is applied to the vitrification mixture on the PES membrane to keep the mRNA-LNP composition from freezing. FIG. 5 sets forth an expected temperature recovery from the initial drop as the vacuum is applied. Once the temperature of the mRNA-LNP plateaus, vitrification is complete. The vitrified mRNA-LNP can then be sealed in an aseptic container, optionally with a desiccant therein until needed. The sealed vitrified product can optionally be stored at room temperature. Once reconstituted, the mRNA-LNP can be expected to have little to no degradation and will demonstrate good antigen presentation when administered in vivo.

Figure 17:
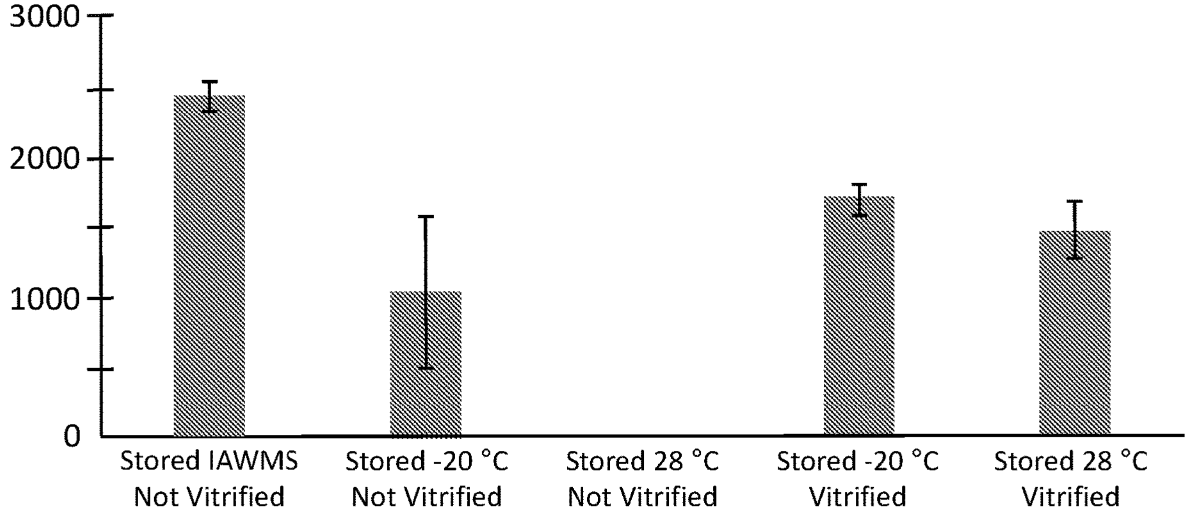
FIG. 17 shows day 3 fluorescence data for the vitrified and unvitrified samples with and Lipofectamine Messenger MAX (Invitrogen), as well as fresh mRNA. Again, the vitrification allowed retention of excellent activity despite the storage conditions, while the unvitrified samples showed significant loss of expression activity.
Figure 18:
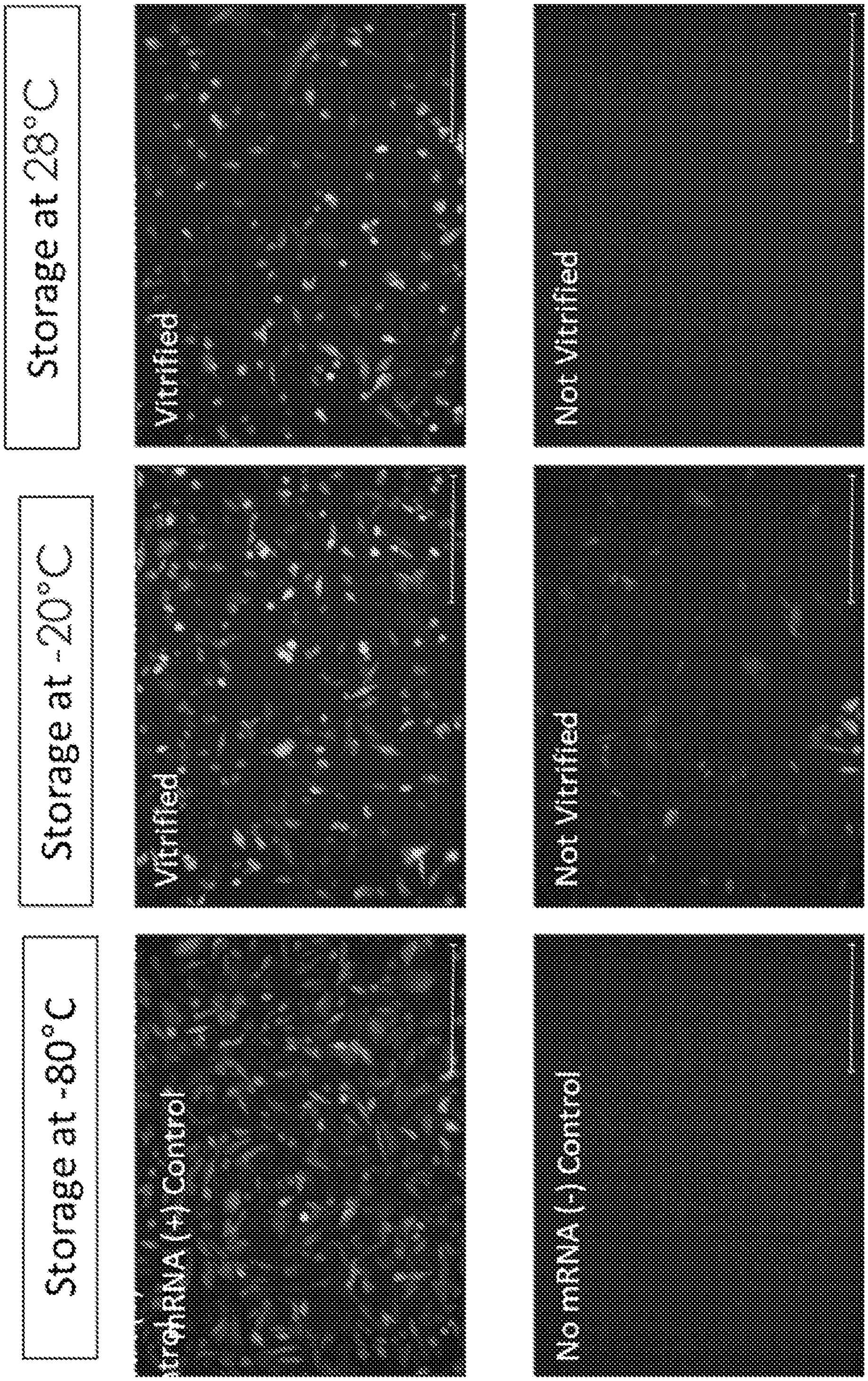
FIG. 18 shows representative images for the fluorescence presented in FIG. 17 with control samples on the left and vitrified samples on the top row with unvitrified samples stored as indicated on the bottom row.

The results of mRNA recovery of the Lipofectamine Messenger MAX (Invitrogen) encapsulated mRNA vitrification/reconstitution are illustrated in FIG. 17. Excellent recovery of mRNA as achieved even with storage at 28° C. whereas without vitrification, all mRNA is degraded. As illustrated in FIG. 18, the Lipofectamine Messenger MAX (Invitrogen) encapsulated mRNA vitrified and stored at all temperatures maintained functional activity in the ability to express GFP following transfection of cells.

To further assess the ability to recover mRNA samples from the vitrification process, small volumes of mRNA encoding green fluorescent protein (GFP) were utilized. For the vitrification process, an 8 μm PES membrane (capillary substrate) was first cut into ¼ inch diameter size and autoclaved. A 2× vitrification medium (VM) with contains 1200 mM (or 454 mg/mL) trehalose and 22.7 mg/mL Glycerol in PBS was prepared and then mixed with equal volumes of the mRNA (Dasher GFP mRNA, 3870FS Aldevron) stock. The mixture was allowed to incubate for 5 minutes before pipetting 6 μL to each vitrification capillary substrate. Following pipetting the solution on to the membrane, the samples were covered with a polymer lid and loaded into the vitrification chamber. For each vitrified sample, in total 6 μL was loaded to the membrane before vitrification, within which there was 3 μL of naked mRNA stock, which contains 3 μg of mRNA.

After vitrification, samples were sealed in mylar pouches and stored at 55° C. before testing.

One hundred days after vitrification storage at 55° C., the samples were reconstituted with 50 μL of Fluorobrite media with brief vortexing to release the mRNA. The mRNA was then quantitated using a Take3 plate on a BioTek Synergy H1 microplate reader. Table 2 shows the obtained quantifications.

TABLE 2

| Samples | 260/280 ratio | Concentration (ng/μL) |
|---|---|---|
| Positive Control (Fresh mRNA) | 2.02 | 67.28 |
| Vitrified mRNA on PES membrane and stored at 55° C. for 100 days | 2.19 | 64.36 |

Portions of the mRNA were then used for transfection or for visualization on an agarose gel.

Figure 19:
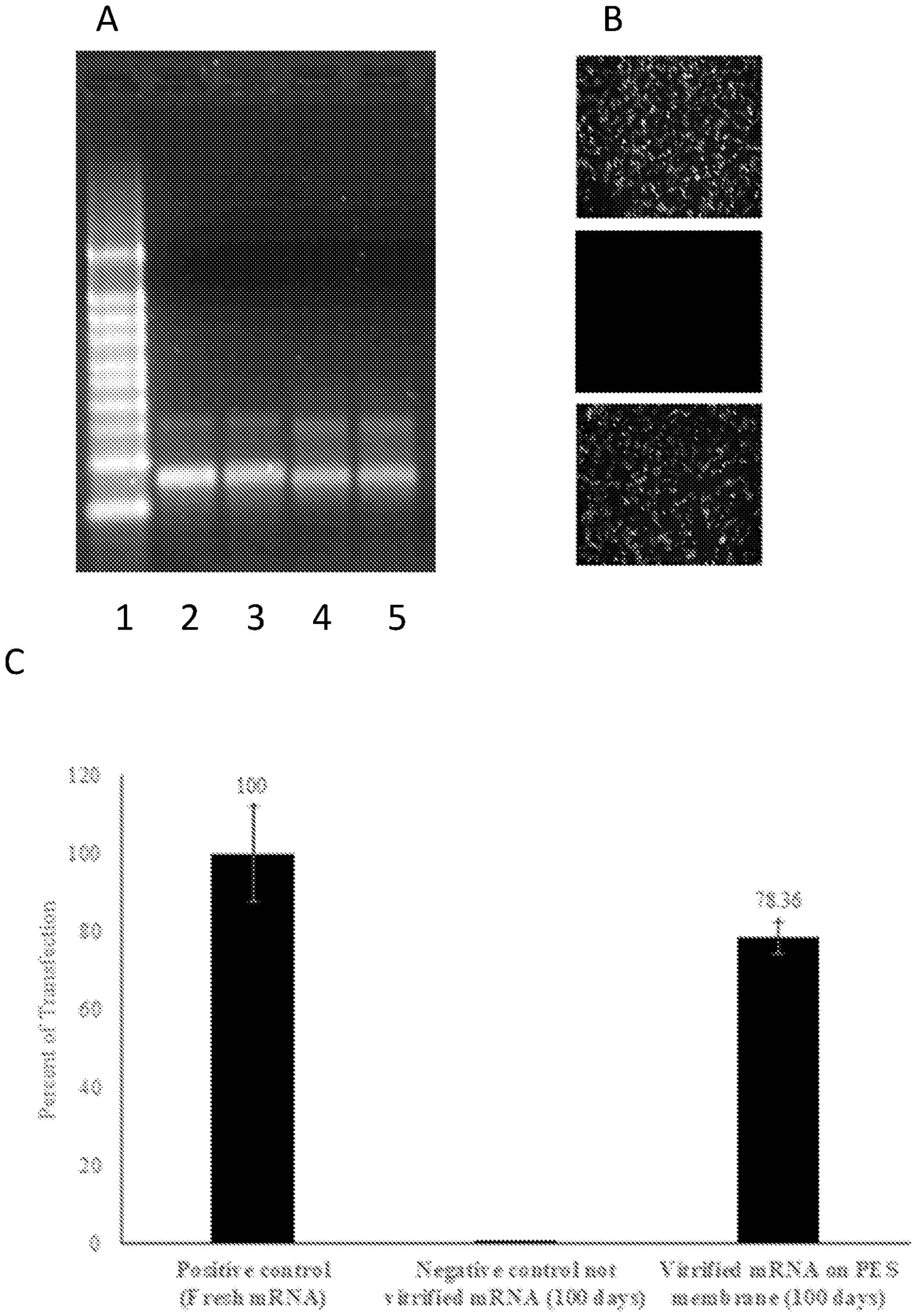
FIG. 19 shows successful reconstitution and retained functionality of vitrified mRNA from a low starting volume. (A) shows an agarose gel depicting liquid mRNA (lanes 2 and 3), reconstituted mRNA (lanes 4 and 5) and mRNA not vitrified by subjected to the same storage conditions (lanes 5 and 6). (B) shows expressed green fluorescent protein (GFP) following transfection with fresh mRNA (top), non-vitrified mRNA (middle) and reconstituted vitrified mRNA (bottom). (C) shows the percent of fluorescence of GFP relative to the positive control. The vitrification process did not negatively impact the amount of mRNA recovered or the functionality thereof.

For the agarose gel, a ladder of 3 μL of Millennium™ RNA Markers (AM7150) with 3 L of dye and 5 μL of water was used in the first lane of a 1.2% agarose gel. For a positive control the stock mRNA was diluted to 125 ng/μL with 3 positive control: dilute mRNA stock to 125 ng/L then 1 μL of the diluent stock was mixed with 3 μL of dye and 5 μL of water. For the vitrified samples 125 ng of reconstituted mRNA was mixed with 3 μL of dye and 5 μL of water. After running the gel at 85V for an hour, the gel was stained with SYBR Green II for 30 mins on a shaker read in a BioRad transilluminator. FIG. 19A shows a captured image of the gel with lanes 2 and 3 being fresh mRNA that was stored at −80° C., lanes 4 and 4 being reconstituted vitrified mRNA and 5 and 6 being non-vitrified mRNA stored at 55° C.

For transfection, a positive control of 4 μL lipofectamine (Lipofectamine™ MessengerMAX™ Transfection Reagent, Lipofectamine™ MessengerMAX™ Transfection Reagent) was added to 16 μL media, allowed to incubate for 10 minutes. In another tube, 1 μL of mRNA (fresh sample) was added to 19 μL of media and incubated for 10 mins. The two solutions were then mixed and incubated for another 5 minutes before transferring 10 μL cell plates seeded with 0.9×106 cells/mL CHO (Chinese hamster ovary) cells. For a negative control and for the vitrified samples, after quantification the volume of mRNA was normalized to that required to make 1 μg of mRNA and added to lipofectamine after a 10-minute incubation. FIG. 19B shows collected images of GFP expression, with the tope panel being the positive control of fresh mRNA, the middle being the negative control of non-vitrified mRNA stored at 55° C., and the bottom panel being reconstituted mRNA. FIG. 19C shows the obtained percentage of transfection efficiency relative to that obtained with the positive control.

The mRNA vitrified on the PES membrane and stored at 55° C. for 100 days maintains the mRNA integrity, purity, and stability similar to the fresh liquid mRNA that was stored at −80° C.

Encapsulated RNA

It was next assessed as to how both a carrier and an encapsulated nucleic acid would fare when reconstituted from the vitrification processes described herein. Vitrification of a Lentivirus was selected due to it providing an encapsulating membrane that contains lipids, carbohydrates and proteins, as well as providing an encapsulated nucleic acid within each virion.

Lentivirus (Lenti-ORF Control Particles (pLenti-C-mGFP), Origene, Cat PS100071V5I) was prepared immediately before use. The potential influence of filter and storage temperature were addressed. The MOI (multiplicity of infection) used for the Lentivirus is 4 and for 25,000 seeded cells/well, 10 μL virus stock was required/well. Lentivirus was mixed with a vitrification medium of 1200 mM trehalose and 10% w/v glycerol in equal volumes (10 μL and 10 μL) to prepare each sample. Aliquots (10 μL) from each sample were provided to either 24 hr room temperature water washed PES membrane (10 mm) or sterile water and PBST washed naked filter (10 mm). The PES membranes were prepared by cutting PES (10 mm diameter), washing in water at RT 24 h, drying for 1 h at 37° C. and then autoclaving. The naked filters were prepared by cutting naked filter (10 mm diameter), washing in water at RT 10 mins, then washing in PBST 0.05% for 10 mins at RT, drying for 1 h at 37° C. and then autoclaving.

Vitrification was for 30 mins with a heat bed temperature set at 37° C. Following vitrification stored at 24° C. or 37° C. for 1, 2, and 3 weeks. Negative controls of Lentivirus alone were stored for 1, 2, and 3 weeks at both 24° C. or 37° C. Similarly negative controls of Lentivirus in vitrification medium (not vitrified) were also stored for 1, 2, and 3 weeks at both 24° C. or 37° C.

For transduction, one day prior, 25,000 cells (HEK 293) were seeded on a 96 well Costar black with clear flat bottom assay plate. On the day of transduction, cell confluency was confirmed with microscope (70% or more). For the positive controls 30 μL of lentivirus was mixed with 570 μL of C-EMEM and 200 μl was added to each well. For vitrified samples, two vitrified samples were eluted in 275 μL of C-EMEM and the cells were transduced in the well with the eluted solution. For the negative control only, 30 μL of lentivirus was mixed with 570 μL of C-EMEM, and then 200 μL of negative control solution was added to each well to transduce the cells. For the negative control with the vitrification medium, 30 μL of lentivirus+30 μL of the vitrification medium were added to 540 μL of C-EMEM, and then 200 μL of negative control solution was added to each well to transduce the cells. Plates were incubated for 72 hr at 37° C. After the incubation, pictures of the post-transduction were taken using the fluorescent microscope and GFP expression was measured with the plate reader.

Figure 20:
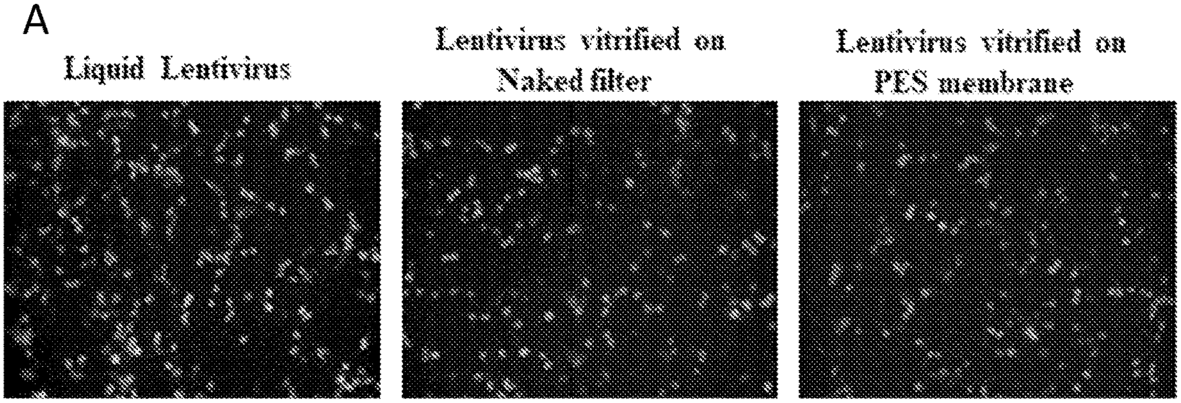
FIG. 20 shows Lentivirus vitrified on water washed PES membrane or PBS-T washed naked filter, and fresh liquid lentivirus samples were transduced on HEK293 cells and incubated for 72 h. (A) shows images taken using fluorescence microscopy after post-transduction. (B) shows percentage of transduction efficiency based fluorescence intensity measured using a fluorescence plate reader and represents the percentage of transduction respective to the liquid lentivirus positive control. When cells were transduced immediately after vitrification, vitrified lentivirus performed as well as liquid lentivirus stored at −80° C. regardless of the scaffold used (Naked filter or PES), indicating that the vitrification process did not damage the particles.
Figure 20:
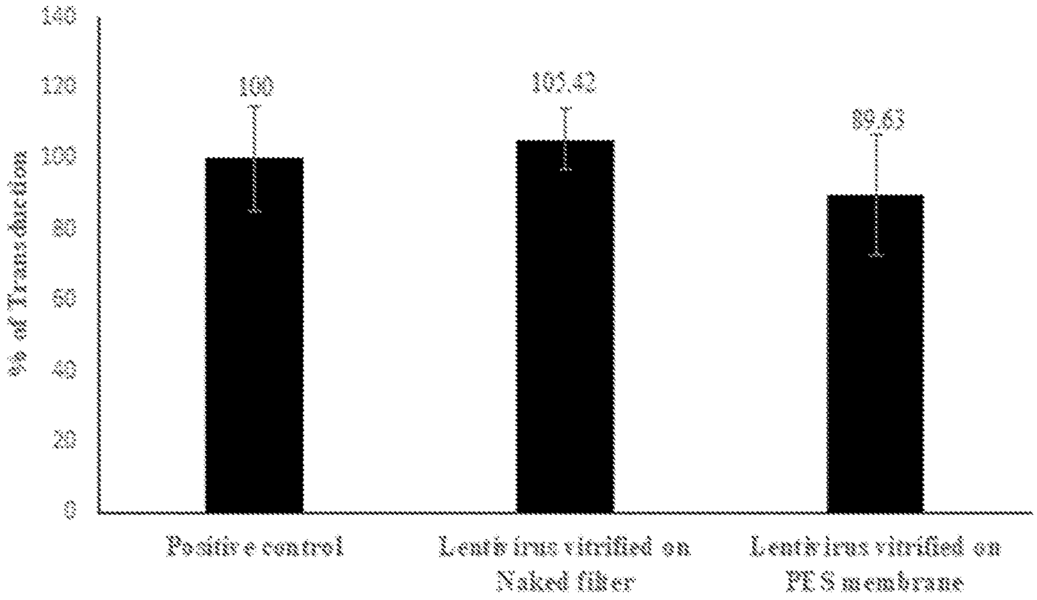

FIG. 20 shows both images of GFP expression (FIG. 20A) and percent of transduction (FIG. 20B) for the Lentivirus alone and immediately after vitrification on the naked or PES filters. GFP expression following vitrification on naked filter or PES membrane had a comparable cellular transduction efficiency (based on fluorescence intensity) of fresh liquid lentivirus control. When cells were transduced immediately after vitrification, vitrified lentivirus performed as well as liquid lentivirus stored at −80° C. regardless of the scaffold used (Naked filter or PES), indicating that the vitrification process did not damage the particles.

Figure 21:
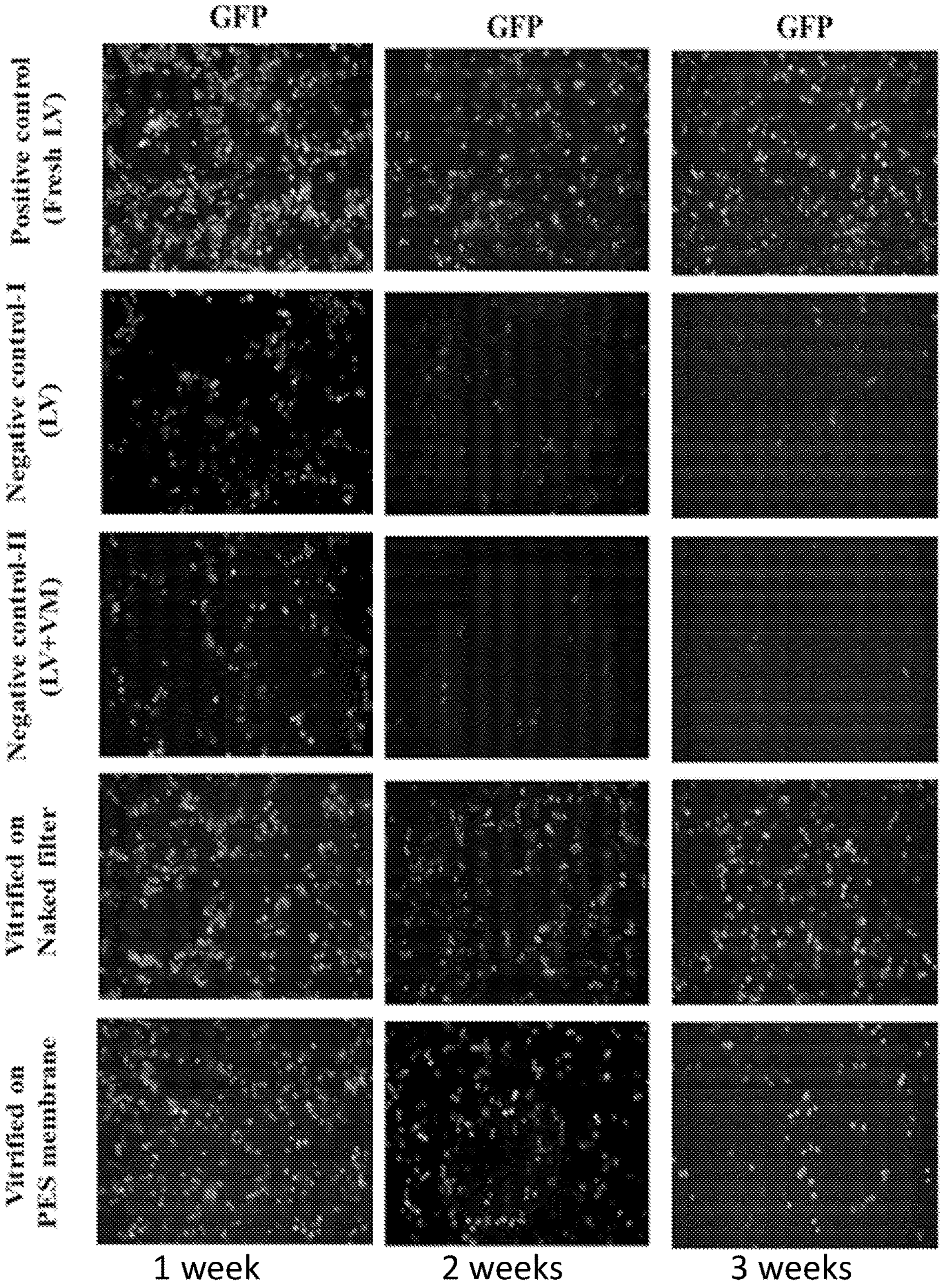
FIG. 21 shows Lentivirus vitrified on water washed PES membrane or PBS-T washed naked filter, and the negative controls (not vitrified) were stored at 24° C. for one week, two weeks or 3 weeks. The fresh liquid lentivirus, vitrified and not vitrified negative control samples were transduced on HEK293 cells and incubated for 72 h. After post-transduction images were taken using fluorescence microscopy. Liquid lentivirus stored at −80° C. is indicated as the "Positive Control." Not vitrified liquid lentivirus stored at 24° C. for 1 week is indicated as the "Negative Control-I" (virus alone) and "Negative Control-II" (virus and vitrification medium)
Figure 22A:
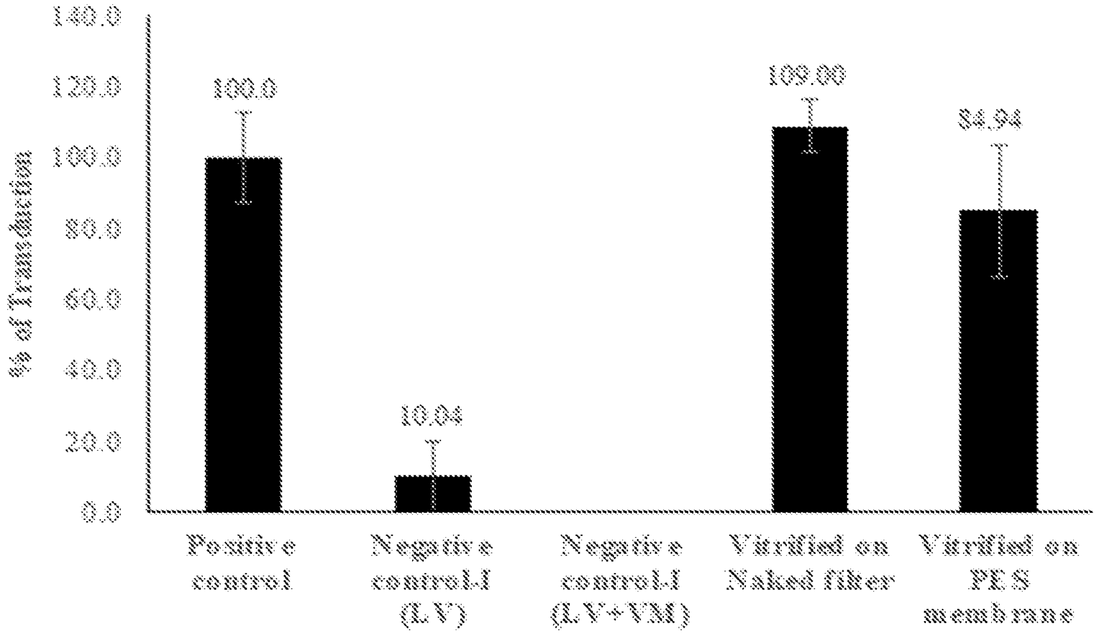
FIG. 22A shows the 2 week storage at 24° C. percentage of transduction efficiency based fluorescence intensity was measured using fluorescence plate reader and represented the percentage of transduction respective to the liquid lentivirus positive control.
Figure 22B:
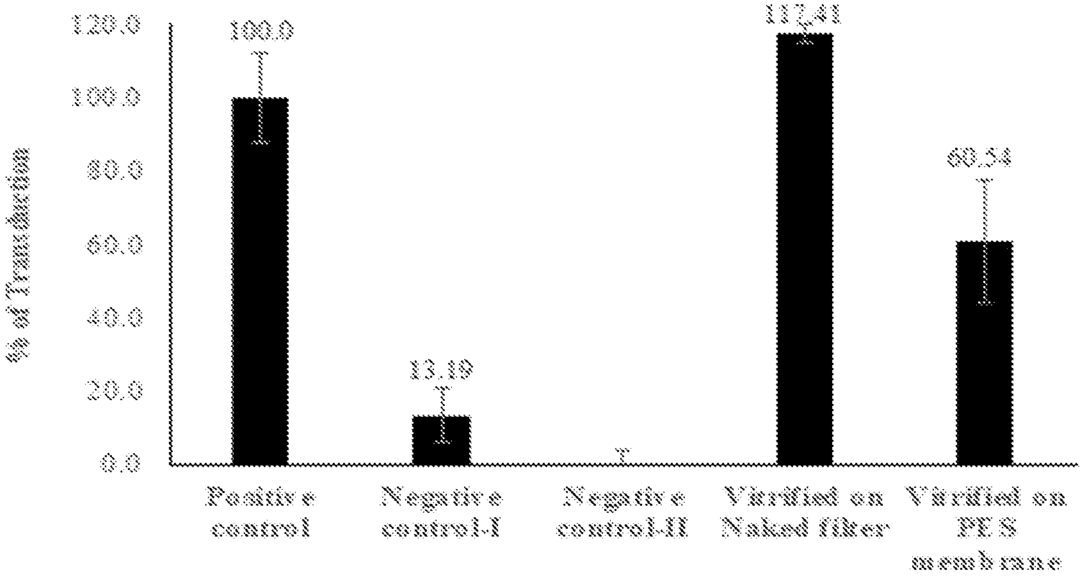
FIG. 22B shows the same from FIG. 22A following 3 weeks of storage at 24° C.

FIG. 21 shows GFP expression at 1, 2, and 3 weeks following storage at 24° C. FIG. 22 shows percentage of transduction efficiency based on fluorescence intensity measured and set respective to the liquid lentivirus positive control after 2 weeks (FIG. 22A) and 3 weeks (FIG. 22B) storage at 24° C. Vitrified lentivirus, regardless of the scaffold used (Naked Filter or PES), retained its functional activity by all 3 measures despite storage at 24° C. for 3 weeks whereas the negative controls demonstrated a significant reduction in function.

Figure 23:
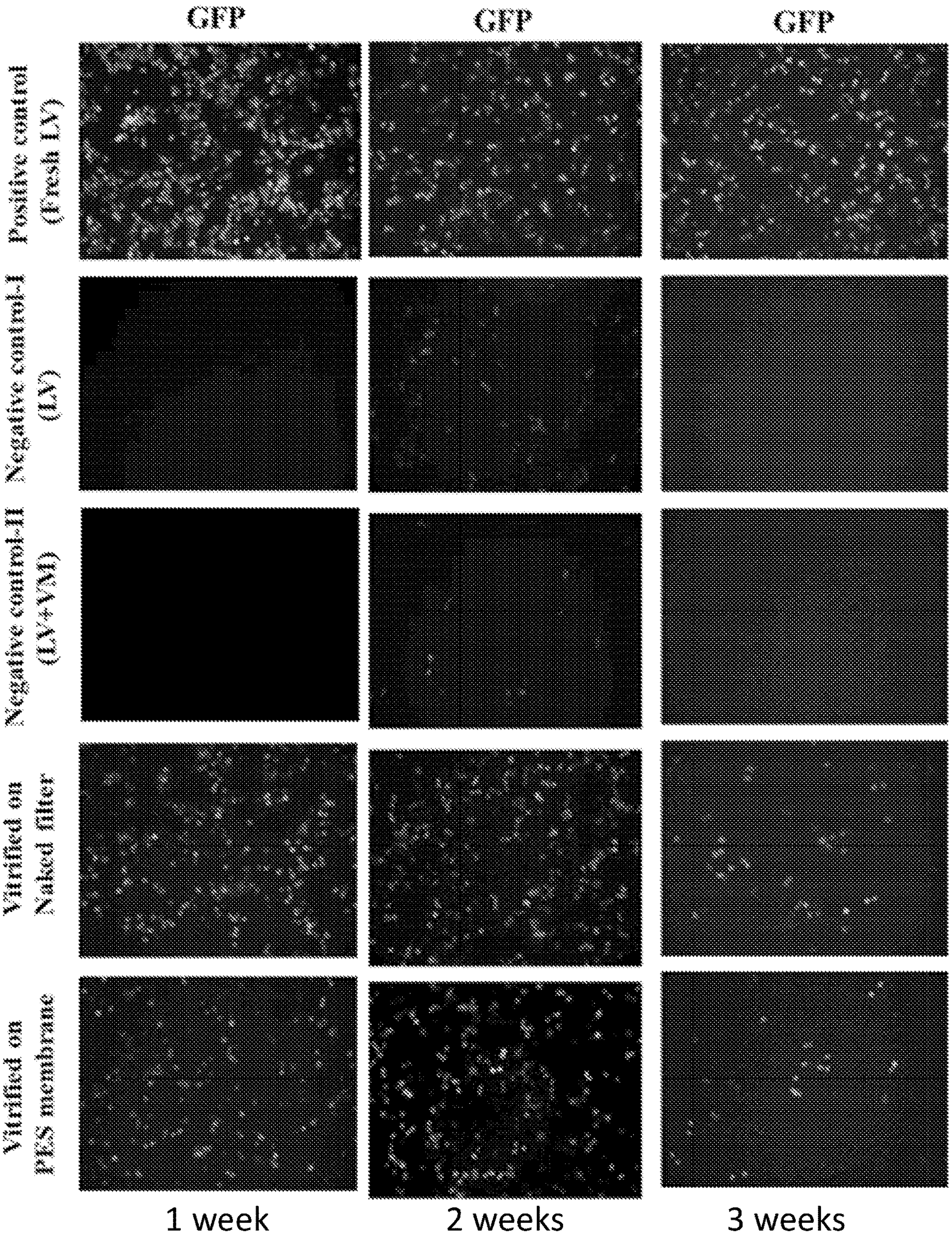
FIG. 23 shows Lentivirus vitrified on water washed PES membrane or PBS-T washed naked filter, and the negative controls (not vitrified) were stored at 37° C. for one week, two weeks and 3 weeks. The fresh liquid lentivirus, vitrified and not vitrified negative control samples were transduced on HEK293 cells and incubated for 72 h. After post-transduction images were taken using fluorescence microscopy. Liquid lentivirus stored at −80° C. is indicated as the "Positive Control." Not vitrified liquid lentivirus stored at 24° C. for 1 week is indicated as the "Negative Control-I" (virus alone) and "Negative Control-II" (virus and vitrification medium).
Figure 24A:
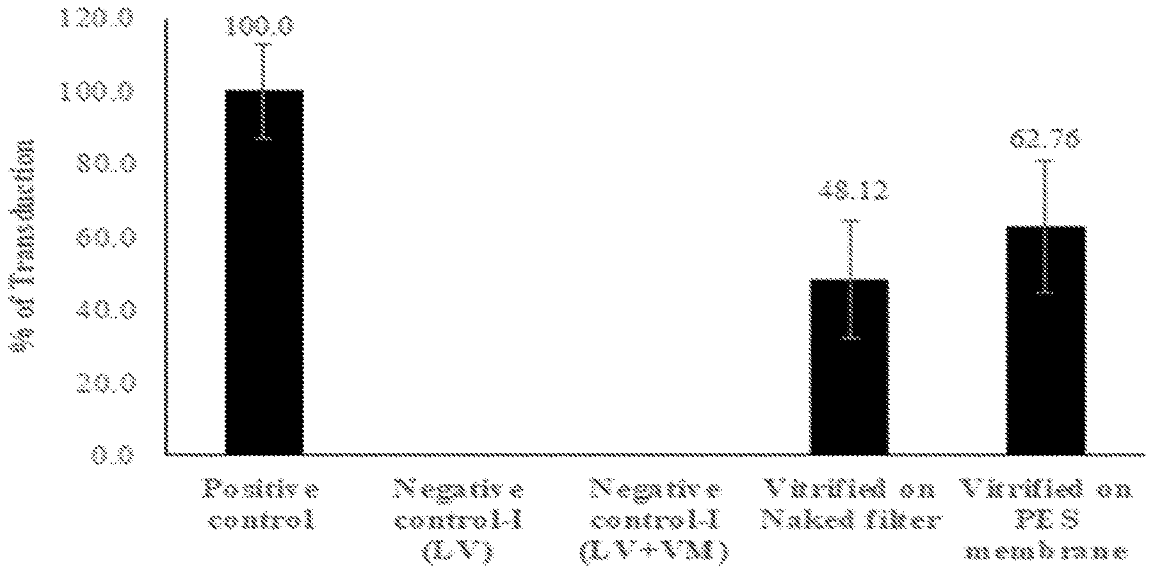
FIG. 24A shows the 2 week storage at 37° C. percentage of transduction efficiency based fluorescence intensity was measured using fluorescence plate reader and represented the percentage of transduction respective to the liquid lentivirus positive control.
Figure 24B:
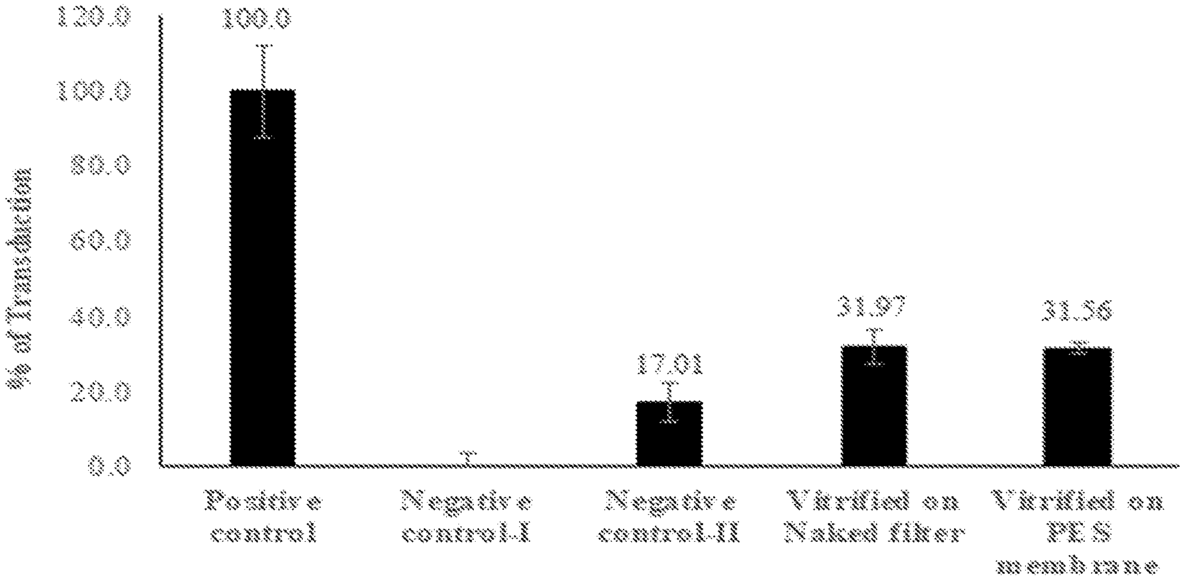
FIG. 24B shows the same as FIG. 24A following 3 weeks of storage at 37° C.

Similarly, FIG. 23 shows GFP expression at 1, 2, and 3 weeks following storage at 37° C. and FIG. 24 shows percentage of transduction efficiency based on fluorescence intensity measured and set respective to the liquid lentivirus positive control after 2 weeks (FIG. 24A) and 3 weeks (FIG. 24B) storage at 37° C. Vitrified lentivirus, regardless of the scaffold used (Naked Filter or PES), retained its functional activity by all 3 measures despite storage at 37° C. for 3 weeks whereas the negative controls demonstrated a significant reduction in function.

FURTHER EXAMPLES

A first aspect of the present disclosure, either alone or in combination with any other aspect herein, concerns a process for vitrification of one or more particles above cryogenic temperature, the process comprising: a) placing a vitrification mixture comprising a particle thereof and a vitrification medium in or on a substrate comprising or forming a capillary network, and placing said substrate in a desiccation chamber; b) lowering the atmospheric pressure within the desiccation chamber; c) providing a heat energy to the lipid particle, wherein the heat energy is sufficient to prevent the vitrification mixture from experiencing freezing conditions; and d) desiccating the vitrification mixture by capillary action until the vitrification mixture enters a glassy state.

A second aspect of the present disclosure, either alone or in combination with any other aspect herein, concerns the process of the first aspect, wherein the particle comprises a polynucleotide.

A third aspect of the present disclosure, either alone or in combination with any other aspect herein, concerns the process of the second aspect, wherein the polynucleotide comprises an mRNA and wherein the mRNA is encapsulated within the particle.

A fourth aspect of the present disclosure, either alone or in combination with any other aspect herein, concerns the process of any one the first through third aspects, wherein the particle comprises a viral capsid, viral envelope, or portion thereof.

A fifth aspect of the present disclosure, either alone or in combination with any other aspect herein, concerns the process of any one the first through third aspects, wherein the particle further comprises a cell penetrating peptide or a carrier protein.

A sixth aspect of the present disclosure, either alone or in combination with any other aspect herein, concerns the process of the fifth aspect, wherein the cell penetrating peptide or the carrier protein is coupled to the polynucleotide.

A seventh aspect of the present disclosure, either alone or in combination with any other aspect herein, concerns the process of the second or third aspects, wherein the polynucleotide is encapsulated by a lipid membrane comprised of a cationic lipid and/or an ionizable lipid.

An eighth aspect of the present disclosure, either alone or in combination with any other aspect herein, concerns the process of any one of the first through third aspects, wherein the capillary network is provided by contours along the surface of the substrate.

A ninth aspect of the present disclosure, either alone or in combination with any other aspect herein, concerns the process of any one of the first through third aspects, wherein the substrate is a wall of the desiccation chamber or is associated with a wall of the desiccation chamber.

A tenth aspect of the present disclosure, either alone or in combination with any other aspect herein, concerns the process of any the first through third aspects, wherein the capillary network within the desiccation chamber is supported by an underlying solid support substrate.

An eleventh aspect of the present disclosure, either alone or in combination with any other aspect herein, concerns the process of any one of the first through third aspects, wherein vitrification of the vitrification mixture occurs in less than 30 minutes.

A twelfth aspect of the present disclosure, either alone or in combination with any other aspect herein, concerns the process of the eleventh aspect, wherein vitrification of the vitrification mixture occurs in less than 10 minutes.

A thirteenth aspect of the present disclosure, either alone or in combination with any other aspect herein, concerns the process of any one of the first through third aspects, wherein the heat energy is provided by heating the vitrification mixture.

A fourteenth aspect of the present disclosure, either alone or in combination with any other aspect herein, concerns the process of any one of the first through third aspects, wherein the atmospheric pressure is lowered to a value of from about 0.9 atm to about 0.005 atm.

A fifteenth aspect of the present disclosure, either alone or in combination with any other aspect herein, concerns the process of the fourteenth aspect, wherein the atmospheric pressure is lowered to about 0.004 atm.

A sixteenth aspect of the present disclosure, either alone or in combination with any other aspect herein, concerns the process of any one of the first through third aspects, wherein the heat energy provided is sufficient to prevent crystallization within the vitrification mixture during vitrification.

A seventeenth aspect of the present disclosure, either alone or in combination with any other aspect herein, concerns the process of any one of the first through third aspects, wherein the provided heat energy is sufficient to keep the biological sample at a temperature of from about 0° C. to about 40° C. during said vitrifying.

An eighteenth aspect of the present disclosure, either alone or in combination with any other aspect herein, concerns the process of any one of the first through third aspects, wherein said vitrification medium comprises a disaccharide, optionally trehalose, glycerol and betine and/or choline.

A nineteenth aspect of the present disclosure, either alone or in combination with any other aspect herein, concerns the process of any one of the first through third aspects, wherein the capillary network is hydrophilic.

A twentieth aspect of the present disclosure, either alone or in combination with any other aspect herein, concerns the process of any one of the first through third aspects, wherein the capillary network comprises contiguous capillary channels.

A twenty-first aspect of the present disclosure, either alone or in combination with any other aspect herein, concerns the process of any one of the first through third aspects, wherein the particle composition is stored after vitrification for a period of at least three weeks at a temperature of 60° C. or lower.

A twenty-second aspect of the present disclosure, either alone or in combination with any other aspect herein, concerns the process of the twenty first aspect, wherein the particle is reconstituted in an aqueous medium and retains equivalent or near equivalent activity as the particle or contents thereof prior to step a).

A twenty-third aspect of the present disclosure, either alone or in combination with any other aspect herein, concerns the process of any one of the first through third aspects, wherein the vitrification medium comprises trehalose and glycerol suspended in a cellular media.

A twenty-fourth aspect of the present disclosure, either alone or in combination with any other aspect herein, concerns the process of the twenty third aspect, wherein the vitrification medium comprises from 500 to 1500 mM trehalose and from 5 to 20 percent weight by volume of glycerol in the cellular media.

A twenty-fifth aspect of the present disclosure, either alone or in combination with any other aspect herein, concerns the process of any one of the first through third aspects, further comprising placing the capillary network following step d) in a dark environment.

A twenty-sixth aspect of the present disclosure, either alone or in combination with any other aspect herein, concerns the process of the twenty-fifth aspect, wherein the dark environment is maintained with an atmosphere of below 5% relative humidity (RH).

A twenty-seventh aspect of the present disclosure, either alone or in combination with any other aspect herein, concerns the process of the twenty-sixth aspect, wherein the dark environment is maintain at 2% RH or lower.

A twenty-eighth aspect of the present disclosure, either alone or in combination with any other aspect herein, concerns a method for inducing an immune response in a subject, comprising: a) reconstituting the vitrification mixture obtained from any of the first through twenty-seventh aspects by providing a volume of a solution to the vitrification mixture on the capillary network to obtain an eluted vitrification mixture; b) obtaining the eluted vitrification mixture from the capillary network; and c) administering the eluted vitrification mixture to the subject.

A twenty-ninth aspect of the present disclosure, either alone or in combination with any other aspect herein, concerns the method of the twenty-eighth aspect, wherein the particle comprises an attenuated virus.

A thirtieth aspect of the present disclosure, either alone or in combination with any other aspect herein, concerns the method of the twenty-eighth aspect, wherein the particle comprises a polynucleotide, optionally an mRNA, encoding at least a portion of a viral protein.

A thirty-first aspect of the present disclosure, either alone or in combination with any other aspect herein, concerns the method of the thirtieth aspect, wherein the polynucleotide is coupled to a cell penetrating peptide.

A thirty-second aspect of the present disclosure, either alone or in combination with any other aspect herein, concerns the method of the thirty-first aspect, wherein the polynucleotide is encapsulated by a lipid membrane.

A thirty-third aspect of the present disclosure, either alone or in combination with any other aspect herein, concerns the method of the thirty-first aspect, wherein the lipid membrane comprises a cationic lipid.

A thirty-fourth aspect of the present disclosure, either alone or in combination with any other aspect herein, concerns the method of the thirty-first aspect, wherein the lipid membrane comprises an ionizable lipid.

A thirty-fifth aspect of the present disclosure, either alone or in combination with any other aspect herein, concerns a vitrified polynucleotide composition comprising a polynucleotide molecule encapsulated in a particle, and a dehydrated vitrification medium.

A thirty-sixth aspect of the present disclosure, either alone or in combination with any other aspect herein, concerns the vitrified vaccine composition of the thirty-fifth aspect, wherein the composition is vitrified without freezing the polynucleotide molecule.

A thirty-seventh aspect of the present disclosure, either alone or in combination with any other aspect herein, concerns the vitrified vaccine composition of the thirty-fifth aspect, wherein the particle comprises an attenuated virus.

A thirty-eighth aspect of the present disclosure, either alone or in combination with any other aspect herein, concerns the vitrified vaccine composition of any one of the thirty-fifth through thirty-seventh aspects, wherein the polynucleotide molecule comprises an mRNA encoding at least a portion of a viral protein.

A thirty-ninth aspect of the present disclosure, either alone or in combination with any other aspect herein, concerns he vitrified vaccine composition of any one of the thirty-fifth through thirty-seventh aspects, wherein the polynucleotide molecule is coupled to a cell penetrating peptide.

A fortieth aspect of the present disclosure, either alone or in combination with any other aspect herein, concerns the vitrified vaccine composition of any one of the thirty-fifth through thirty-seventh aspects, wherein the particle comprises a cationic lipid.

A forty-first aspect of the present disclosure, either alone or in combination with any other aspect herein, concerns a kit for providing an immune response in a subject, comprising the vitrified mixture made by any one of the first through twenty-seventh aspects.

A forty-second aspect of the present disclosure, either alone or in combination with any other aspect herein, concerns the kit of the forty-first aspect, wherein the vitrified mixture is stored in a dark, desiccated container.

A forty-third aspect of the present disclosure, either alone or in combination with any other aspect herein, concerns the kit of the forty-first aspect, further comprising a sterile solvent suitable to reconstitute the vitrified mixture, the solvent suitable for administration to a subject.

A forty-fourth aspect of the present disclosure, either alone or in combination with any other aspect herein, concerns the kit of any one of the forty-first through forty-third aspects, further comprising a vial.

Various modifications of the present disclosure, in addition to those shown and described herein, will be apparent to those skilled in the art of the above description. Such modifications are also intended to fall within the scope of the appended claims.

It is appreciated that all reagents are obtainable by sources known in the art unless otherwise specified.

It is also to be understood that this disclosure is not limited to the specific aspects and methods described herein, as specific components and/or conditions may, of course, vary. Furthermore, the terminology used herein is used only for the purpose of describing particular aspects of the present disclosure and is not intended to be limiting in any way. It will be also understood that, although the terms "first," "second," "third" etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, "a first element," "component," "region," "layer," or "section" discussed below could be termed a second (or other) element, component, region, layer, or section without departing from the teachings herein. Similarly, as used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

Reference is made in detail to exemplary compositions, aspects and methods of the present disclosure, which constitute the best modes of practicing the disclosure presently known to the inventors. The Figures are not necessarily to scale. However, it is to be understood that the disclosed aspects are merely exemplary of the disclosure that may be embodied in various and alternative forms. Therefore, specific details disclosed herein are not to be interpreted as limiting, but merely as a representative basis for any aspect of the disclosure and/or as a representative basis for teaching one skilled in the art to variously employ the present disclosure.

Patents, publications, and applications mentioned in the specification are indicative of the levels of those skilled in the art to which the disclosure pertains. These patents, publications, and applications are incorporated herein by reference to the same extent as if each individual patent, publication, or application was specifically and individually incorporated herein by reference.

The foregoing description is illustrative of particular embodiments of the disclosure, but is not meant to be a limitation upon the practice thereof. The following claims, including all equivalents thereof, are intended to define the scope of the disclosure.

We claim:

1. A process for vitrification of one or more particles above cryogenic temperature, the process comprising:

a) placing a vitrification mixture comprising a particle thereof and a vitrification medium in or on a substrate comprising or forming a capillary network, and placing said substrate in a desiccation chamber, wherein the particle comprises: a viral capsid, viral envelope, or portion thereof; or a lipid particle;

b) lowering an atmospheric pressure within the desiccation chamber;

c) providing a heat energy to the particle, wherein the heat energy is sufficient to prevent the vitrification mixture from experiencing freezing conditions;

d) desiccating the vitrification mixture by capillary action until the vitrification mixture enters a glassy state;

e) storing the vitrification mixture for a period of at least three weeks at a temperature equal to or less than 60° C.; and f) reconstituting the particle in an aqueous medium, wherein the particle retains equivalent activity as the particle or contents thereof prior to step a).

2. The process of claim 1, wherein the particle further comprises a cell penetrating peptide or a carrier protein, wherein the cell penetrating peptide or the carrier protein is coupled to a polynucleotide.

3. The process of claim 1, wherein the particle comprises a polynucleotide encapsulated by a lipid membrane comprised of the lipid.

4. The process of claim 1, wherein the capillary network is provided by contours along a surface of the substrate.

5. The process of claim 1, wherein the substrate is a wall of the desiccation chamber or is associated with a wall of the desiccation chamber.

6. The process of claim 1, wherein the capillary network within the desiccation chamber is supported by an underlying solid support substrate.

7. The process of claim 1, wherein vitrification of the vitrification mixture occurs in less than 30 minutes.

8. The process of claim 1, wherein the heat energy is provided by heating the vitrification mixture.

9. The process of claim 1, wherein the atmospheric pressure is lowered to a value of from 0.9 atm to 0.005 atm.

10. The process of claim 1, wherein the heat energy provided is sufficient to prevent crystallization within the vitrification mixture during vitrification.

11. The process of claim 1, wherein the provided heat energy is sufficient to keep the vitrification mixture at a temperature of from 0° C. to 40° C. during said vitrifying.

12. The process of claim 1, wherein the vitrification medium comprises trehalose and glycerol suspended in a cellular media.

13. A method for inducing an immune response in a subject, comprising:

a) reconstituting the vitrification mixture obtained from claim 1 by providing a volume of a solution to the vitrification mixture on the capillary network to obtain an eluted vitrification mixture;

b) obtaining the eluted vitrification mixture from the capillary network; and c) administering the eluted vitrification mixture to the subject.

14. The method of claim 13, wherein the particle comprises: an attenuated virus; a polynucleotide encoding at least a portion of a viral protein; a cell penetrating peptide; or a combination thereof.

15. The method of claim 14, wherein the polynucleotide is encapsulated by a lipid membrane.

16. The method of claim 15, wherein the lipid membrane comprises a cationic lipid, an ionizable lipid, or a combination thereof.

17. A vitrified polynucleotide composition comprising a polynucleotide molecule encapsulated in a particle, and a dehydrated vitrification medium.

* * * * *